(12) United States Patent
Durand et al.

(10) Patent No.: US 11,471,672 B2
(45) Date of Patent: Oct. 18, 2022

(54) NEURAL ELECTRODES AND METHODS FOR IMPLANTING SAME

(71) Applicant: Case Western Reserve University, Cleveland, OH (US)

(72) Inventors: Dominique M. Durand, Cleveland, OH (US); Grant McCallum, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 1260 days.

(21) Appl. No.: 15/756,708

(22) PCT Filed: Sep. 8, 2016

(86) PCT No.: PCT/US2016/050609
§ 371 (c)(1),
(2) Date: Mar. 1, 2018

(87) PCT Pub. No.: WO2017/044519
PCT Pub. Date: Mar. 16, 2017

(65) Prior Publication Data
US 2018/0264255 A1    Sep. 20, 2018

Related U.S. Application Data

(60) Provisional application No. 62/215,395, filed on Sep. 8, 2015.

(51) Int. Cl.
*A61N 1/05* (2006.01)
*A61B 5/00* (2006.01)
(Continued)

(52) U.S. Cl.
CPC .............. *A61N 1/0558* (2013.01); *A61B 5/24* (2021.01); *A61B 5/296* (2021.01); *A61B 5/389* (2021.01);
(Continued)

(58) Field of Classification Search
CPC ... A61F 2/72; A61B 5/296389; A61B 5/6882; A61B 5/6877; A61B 2562/125; A61B 5/296; A61B 5/389; A61N 1/0558
See application file for complete search history.

(56) References Cited

U.S. PATENT DOCUMENTS

| | | | |
|---|---|---|---|
| 4,374,527 A * | 2/1983 | Iversen | A61N 1/056 607/117 |
| 7,162,310 B2 * | 1/2007 | Doan | A61N 1/0573 607/127 |

(Continued)

FOREIGN PATENT DOCUMENTS

WO    2015/157393 A2    10/2015

OTHER PUBLICATIONS

Badia, Jordi, et al. "Biocompatibility of chronically implanted transverse intrafascicular multichannel electrode (TIME) in the rat sciatic nerve." IEEE Transactions on Biomedical Engineering 58.8 (2011): 2324-2332. Abstract Only.

(Continued)

*Primary Examiner* — Eun Hwa Kim
(74) *Attorney, Agent, or Firm* — Tarolli, Sundheim, Covell & Tummino LLP

(57) ABSTRACT

One aspect of the present disclosure can include an intrafascicular neural electrode. The intrafascicular neural electrode can include a microwire body having a proximal end, a distal anchoring end, and a middle portion extending between the proximal end and the distal anchoring end. The distal anchoring end can substantially match the mechanical and biological properties of the target nerve. The microwire body can have a middle anchoring portion extending between the proximal end and the distal end, wherein at least a portion of the distal end and/or the middle anchoring portion substantially match(es) the mechanical and biological properties of the target nerve. The electrode can be made (Continued)

of graphene. The microwire body, except for the distal anchoring end, can be coated with an insulation material, preferably with a biocompatible agent adsorbed onto the insulation material.

10 Claims, 16 Drawing Sheets

(51) Int. Cl.
| | |
|---|---|
| C08G 59/68 | (2006.01) |
| C09J 163/00 | (2006.01) |
| A61B 5/24 | (2021.01) |
| A61B 5/296 | (2021.01) |
| A61B 5/389 | (2021.01) |
| A61L 31/02 | (2006.01) |
| A61L 31/10 | (2006.01) |
| A61F 2/72 | (2006.01) |

(52) U.S. Cl.
CPC .......... *A61B 5/6877* (2013.01); *A61B 5/6882* (2013.01); *A61L 31/024* (2013.01); *A61L 31/10* (2013.01); *A61N 1/0551* (2013.01); *A61N 1/0556* (2013.01); *C08G 59/686* (2013.01); *C09J 163/00* (2013.01); *A61B 2560/063* (2013.01); *A61B 2562/125* (2013.01); *A61F 2/72* (2013.01); *A61L 2400/18* (2013.01)

(56) References Cited

U.S. PATENT DOCUMENTS

| | | | |
|---|---|---|---|
| 9,044,592 B2* | 6/2015 | Imran | ................ A61N 1/0558 |
| 2010/0268055 A1 | 10/2010 | Jung et al. | |
| 2013/0085359 A1 | 4/2013 | Yao et al. | |
| 2015/0141786 A1 | 5/2015 | Durand et al. | |

OTHER PUBLICATIONS

Fattahi, Pouria, et al. "A review of organic and inorganic biomaterials for neural interfaces." Advanced materials 26.12 (2014): 1846-1885.
Lewitus, Dan Y., et al. "Biohybrid carbon nanotube/agarose fibers for neural tissue engineering." Advanced functional materials 21.14 (2011): 2624-2632.
Yoshida, Ken, Thomas Stieglitz, and Shaoyu Qiao. "Bioelectric interfaces for the peripheral nervous system." Engineering in Medicine and Biology Society (EMBC), 2014 36th Annual International Conference of the IEEE. IEEE, 2014.
PCT International Search Report and Written Opinion for corresponding International Application No. PCT/US2016/050609, dated Jan. 9, 2017, pp. 1-18.
Chumbimuni-Torres, Karin Y., et al. "Adsorption of proteins to thin-films of PDMS and its effect on the adhesion of human endothelial cells." RSC advances 1.4 (2011): 706-714.
European Examination Report for corresponding European Application Serial No. 16770605.0, dated Mar. 30, 2019, pp. 1-7.

* cited by examiner

NEURAL ELECTRODES AND METHODS FOR IMPLANTING SAME

RELATED APPLICATION

This application claims the benefit of U.S. Provisional Patent Application Ser. No. 62/215,395, filed Sep. 8, 2015, the entirety of which is hereby incorporated by reference for all purposes.

TECHNICAL FIELD

The present disclosure relates generally to neural electrodes and, more particularly, to methods for implanting intrafascicular neural electrodes and methods of using the electrodes, such as recording, measuring and/or stimulating and/or modulating nerve activity.

BACKGROUND

In recent years, advances have been made in the field of neurobiology, in particular in the development of neuroprosthetic devices for motor control. An important aspect in the further advancement of the field and, for example, the control systems for neuroprosthetic devices, will be the ability to obtain stable spatiotemporally distributed recording of neural activity chronically. Another has been in the area of neuromodulation. While the ability to record neural activity plays a critical role in developing this technology, the development of neural interfaces that can provide spatiotemporally distributed stimulation of neural tissue will also be a key to the development of neuroprosthetic/neuromodulation devices.

Typical systems that provide electrical stimulation for neuroprosthetic devices can be applied either on the skin or directly to the nerve. The disadvantages of surface (skin) stimulation include that it is awkward to use and requires that electrodes be placed in the proper location upon every use. Additionally, large currents must be applied with these systems and in people having partial neural sensation, for example, persons with incomplete spinal cord injury, such stimulation can be painful. Implantable electrode systems could overcome some of these problems by being self-contained within the body.

Current nerve interface-based electrodes have several significant technological shortcomings. For example, glass micropipette electrodes can be used as suction electrodes to record and monitor neural activity; however, these electrodes are difficult to establish and secure an adequate fit with the nerve and are too bulky for implantation. More commonly, nerve cuff electrodes are used to record neural activity. Compared to other neural nerve interface based electrodes, the nerve cuff is relatively stable over long-term recording periods. Nevertheless, a major shortcoming of the nerve cuff electrode arises when recording data from a short segment of the nerve, because of the difficulty in placing the electrodes in confined spaces. The nerve cuff can induce changes in the tissue and is covered by connective tissue. The shape of the nerve can change when it completely fills the cuff, which can reduce neural activity over time. Moreover, the signal amplitudes are small and the signal-to-noise ratio is very low. Another type of electrode, the Utah electrode array, which resembles a miniature bed of nails, can only be implanted transversely.

Longitudinal intrafascicular electrodes ("LIFEs") are useful for recording data from sensory fascicles in peripheral nerves, as well as for stimulating motor fascicles also in peripheral nerves. These electrodes are typically made using metallic wires. Polymer based electrodes have also been manufactured and used. Nevertheless, these electrodes are difficult to deploy and use because they need to be threaded through the peripheral nerve and tacked using epineural sutures at both the proximal and distal ends. Additionally, LIFEs can record selectively from a nerve but have not been shown to last for long periods of time. In human experiments, the LIFE electrode could record signals for only 10 days. Furthermore, existing intrafascicular electrodes (e.g., LIFEs) lack compatibility with the mechanical and biological properties of the neural tissue in which they are implanted.

SUMMARY

In one aspect, the present disclosure can relate to an intrafascicular neural electrode. The intrafascicular neural electrode can comprise a microwire body having a proximal end, a distal anchoring end, and a middle portion extending between the proximal end and the distal anchoring end. The distal anchoring end can substantially match the mechanical and biological properties of the target nerve. In some instances, all or only a portion of the microwire body can have a flattened cross-sectional shape. In other instances, the microwire body can be made of graphene.

In another aspect, the present disclosure can include a method for implanting a neural electrode in a fascicle comprising a target nerve. One step of the method can include inserting a microwire assembly into the fascicle. The microwire assembly can comprise a microwire body that substantially matches the mechanical and biological properties of the target nerve and is coiled around a needle introducer. The microwire body can also include an anchoring portion. Next, a portion of the microwire body can be uncoiled from around the needle introducer. The needle introducer can then be withdrawn so that less than the entire anchoring portion of the microwire body remains implanted in the fascicle.

In another aspect, the present disclosure can include a method for implanting a neural electrode in a fascicle comprising a target nerve. One step of the method can include providing a microwire assembly that includes a proximal end, a distal end, and a middle anchoring portion extending between the proximal end and the distal end. At least a portion of the distal end and/or the middle anchoring portion can substantially match the mechanical and biological properties of the target nerve. Next, a portion of the microwire assembly can be inserted into the fascicle so that the distal end, but not the middle anchoring portion, is embedded therein.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

Definitions

Figure 1:
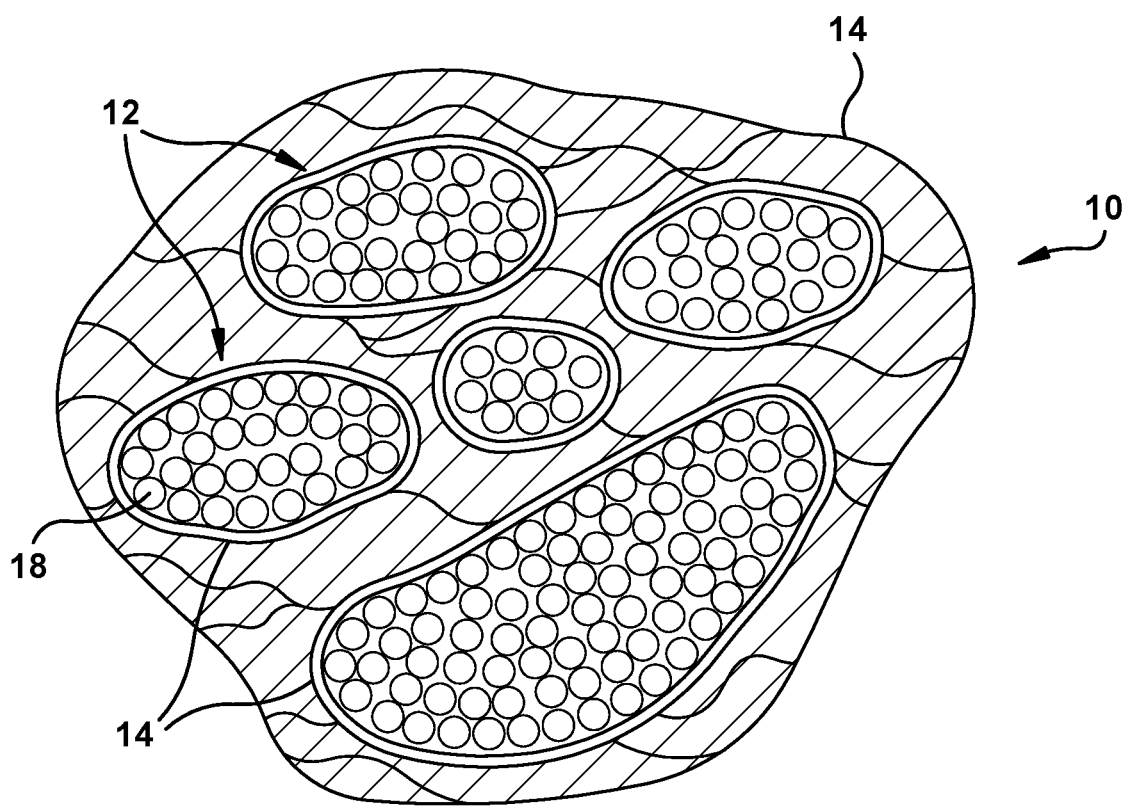
FIG. 1 is a cross-sectional view of a nerve comprising multiple fascicles held together by structural tissue.

Unless otherwise defined, all technical terms used herein have the same meaning as commonly understood by one of ordinary skill in the art to which the present disclosure pertains.

In the context of the present disclosure, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of the apparatus in use or operation in addition to the orientation depicted in the figures. For example, if the apparatus in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

As used herein, the term "subject" can be used interchangeably with the term "patient" and refer to any warm-blooded organism including, but not limited to, human beings, pigs, rats, mice, dogs, goats, sheep, horses, monkeys, apes, rabbits, cattle, etc.

As used herein, the terms "modulate" or "modulating" can refer to causing a change in neuronal activity, chemistry, and/or metabolism. The change can refer to an increase, decrease, or even a change in a pattern of neuronal activity. The terms may refer to either excitatory stimulation (activation) or application of electrical energy that entirely or partially inhibits or blocks nerve activity (e.g., conduction), or a combination thereof. The terms "modulate" or "modulating" can also be used to refer to a masking, altering, overriding, or restoring of neuronal activity.

As used herein, the term "electrical communication" can refer to the ability of a generated electric field to be transferred to, or have an effect on, one or more components of the present disclosure. In some instances, the generated electric field can be directly transferred to a component (e.g., via a wire or lead). In other instances, the generated electric field can be wirelessly transferred to a component. In one example, the term "electrical communication" can refer to the ability of an electric field to be transferred to, or have a neuromodulatory effect, within and/or on at least one nerve, neuron, and/or nervous tissue of a subject.

As used herein, the terms "target nerve" and "target nerve structure" can refer to a cell, nerve, or neural cell can refer to at least one cell comprising the nervous system of an animal (including a human). Thus, the terms "target nerve" or "target nerve structure" can encompass single cells as well as an aggregate of cells that can be part of, or associated with, a neuron or nerve of the peripheral nervous system (PNS) or the central nervous system (CNS) (e.g., the brain or spinal cord), unless specifically noted otherwise. A "nerve" can refer to a bundle of nerve fibers enclosed by a nerve sheath. In some instances, a target nerve structure can refer to the brain of a subject including, but not limited to, the cerebrum, the cerebellum, the limbic system, and the brain stem.

As used herein, the term "peripheral nerve" can refer to a number of fibers of either the somatic or autonomic nervous system, which are not part of the CNS.

As used herein, the term "nerve fascicle" can refer to a plurality of nerve fibers organized and bundled within the lamellated connective tissue (perineurium). A plurality of nerve fascicles can be organized within a protective sheath called the epineurium, forming the peripheral nerve.

As used herein, the term "flexural rigidity" can refer to the amount of resistance a structure offers while undergoing bending. In one example, a mechanical property of a target nerve or target nerve structure can include the flexural rigidity of the target nerve or target nerve structure. A structure's flexural rigidity is calculated to be the product of the material's Young's Modulus (E), and the structure's second moment of inertia ($I_{x,y}$) about an axis. The units of flexural rigidity are in N-m$^2$ and a structure with a lower flexural rigidity is said to be more flexible compared to another. For a structure with a circular cross-section, such as a wire, the second moment of inertia ($I_x=I_y$) is calculated by $(\pi\varphi^4)/64$ where $\varphi$ is the diameter of the wire in meters. For a structure with a rectangular cross-section with a base width (b) and a height (h) in meters, $I_x=(bh^3)/12$ and $I_y=(b^3h)/12$. Finally, for an annulus with an inner radius ($r_1$) and an outer radius ($r_2$) in meters, $I_x=I_y=(\pi/4)*(r_2^2-r_1^2)$. For a thin tube, this can be approximated by $I_x=I_y=(\pi*r^3*t)$ where "r" is the tube radius and "t" is the tube's thickness.

Overview

The present disclosure relates generally to neural electrodes and, more particularly, to methods for implanting intrafascicular neural electrodes and methods of using the electrodes, such as recording, measuring and/or stimulating nerve activity. Although the present disclosure will be describe below mainly in terms of neural electrodes and implantation methods associated with the PNS, it will be appreciated that the present disclosure can also have application to nerves and nerve structures comprising the CNS (e.g., the brain for use in deep brain stimulation).

A nerve 10 (FIG. 1) is composed of one or several fascicles 12 surrounded by a membrane called the epineurium 14. Each fascicle 12 is surrounded by a membrane called the perineurium 16, which is made up of tightly joined cells generating a high impedance barrier. Several hundred axons 18, most of them surrounded by Schwann cells, are packed inside the perineurium 16. The epineurium 14 is made of loose collagen while the perineurium 16 is a protective membrane made of cells with tight junctions that maintain an internal pressure inside the nerve 10 and implement a blood-nerve barrier.

Many approaches have been used to interface with nerves. Penetration of the perineurium 16 must be done with caution, and methods describing such interfaces can be divided in those that do not penetrate the perineurium (outside the nerve) and those that do (inside the nerve). Electrodes placed outside the perineurium 16 typically surround the nerve with a flexible cuff electrode and can be very stable. However, recordings obtained with cuff electrodes have a low signal-to-noise ratio and are not reproducible. Additionally, with wire-based implants (e.g., longitudinal intra-fascicular electrodes or LIFEs), the mechanical compatibility is problematic since the flexural rigidity of the implants was not taken into account. Consequently, such wire-based implants exhibit a lack of longevity and reliability, most likely due to their size and compliance.

Advantageously, the present disclosure provides neural electrodes, systems, methods for implanting the neural electrodes/systems, and associated applications that substantially match the molecular and mechanical properties of the neural electrode to those of a particular target nerve or target nerve structure. This design takes advantage of the low flexural rigidity of the neural electrodes, as well as the biocompatible insulation material comprising the neural electrodes. When implanted in a target nerve or target nerve structure (e.g., a fascicle 12), the neural electrodes of the present disclosure are physically stable and thereby permit chronic recording and/or modulation (e.g., stimulation) of nerve activity. As discussed below, neural electrodes and associated systems of the present disclosure can find use in a variety of clinical and/or research applications, such as recording, measuring and/or stimulating nerve activity.

Neural Electrodes

One aspect of the present disclosure can include a neural electrode 20 (FIGS. 1A-B) configured for implantation into a target nerve or target nerve structure, such as a fascicle 12 of a peripheral nerve. In some instances, the neural electrode 20 can be sized and dimensioned for implantation into a target nerve or target nerve structure comprising the CNS of a subject without damaging the target nerve or target nerve structure. In other instances, the neural electrode 20 can be sized and dimensioned for implantation into a peripheral nerve of a subject without damaging the peripheral nerve. For example, the neural electrode 20 can comprise an intrafascicular neural electrode having dimensions that allow it to fit with the nerve fascicle 12 without damaging the fascicle. The neural electrode 20 can be used in in vivo applications (e.g., either recording or modulation of nerve activity) by, for example, detecting or transmitting electrical impulses. The neural electrode 20 can be placed into electrical communication with any type of device that can record, measure and/or modulate (e.g., stimulate) activity in a target nerve or target nerve structure.

As shown in FIG. 1A, the neural electrode 20 (e.g., an intrafascicular neural electrode) can comprise a microwire body 22 having a proximal end 24, a distal anchoring end 26, and a middle portion 28 extending between the proximal end and the distal anchoring end. In some instances, the distal anchoring end 26 can include that portion of the neural electrode 20 which is implanted within a target nerve or target nerve structure. At least the distal anchoring end 26 (e.g., the entire distal anchoring end or only the distal anchoring end) of the neural electrode 20 can be configured to substantially match the mechanical and biological properties of the target nerve. The term "substantially match" can mean that a particular mechanical and/or biological property of a target nerve or target nerve structure is about 100% (e.g., identical), about 90%, about 80%, about 70%, about 60%, or about 50% or less to a corresponding mechanical and/or biological property of the neural electrode 20 (e.g., the distal anchoring end 26). One example of a mechanical property can include flexural rigidity, which is discussed further herein. One example of a biological property can include the molecular composition and/or associated physiological function of a particular target nerve or target nerve structure, such as the type, amount, and/or function of a particular molecule (e.g., a protein, polysaccharide, proteoglycan, etc.). Thus, in one example, a biological property can refer to the presence of a particular molecule, such as collagen that is present in a fascicle and adsorbed on a neural electrode 20.

The microwire body 22 can be wire-like in shape and dimensions (e.g., long length and thin diameter). It will be appreciated that microwire body 22 need not necessarily have a circular cross-sectional profile. For example, the microwire body 22 can have an oval, square, or rectangular cross-sectional shape. In one example, the microwire body 22 can have a flattened cross-sectional profile and be made of graphene. In some instances, the diameter of the microwire body 22 can be less than, equal to, about equal to, or greater than the diameter of a target nerve or target nerve structure. In one example, the microwire body 22 can have a diameter that is equal to, or about equal to, the diameter of an axon 18 comprising a fascicle 12 of a target nerve or target nerve structure. Advantageously, the relatively small diameter of the microwire body 22 reduces or eliminates damage to the target nerve or target nerve structure while also minimizing a patient's immune reaction to the neural electrode 20.

It will be appreciated that the diameter of the microwire body 22 can vary depending, for example, on the particular type and source of the target nerve or target nerve structure and/or the material(s) used to form the microwire body. In some instances, the microwire body 22 can have a diameter of less than about 5 microns, or about 5 microns to about 25 microns or more (e.g., less than about 10 microns, about 10 microns, or about 25 microns), such as about 30, 40, 50, 60, 70, 80, 90 or 100 microns. In other instances, the microwire body 22 can have a diameter of about 10 microns to about 200 microns. The diameter of the microwire body 22 can be uniform across its entire length or uniform across only a portion of its length. For example, a first portion of the microwire body 22 can have a diameter that is less or greater than the diameter of a different second portion of the microwire body. The microwire body 22 can be made of one or a combination of materials capable of conducting an electrical current therethrough. Examples of such materials can include platinum/iridium, gold, and carbon nanotubes. In one example, the microwire body 22 can be made of carbon nanotubes and have a diameter of less than 10 microns. In some instances, the microwire body 22 can comprise a multichannel wire.

Figure 2A:
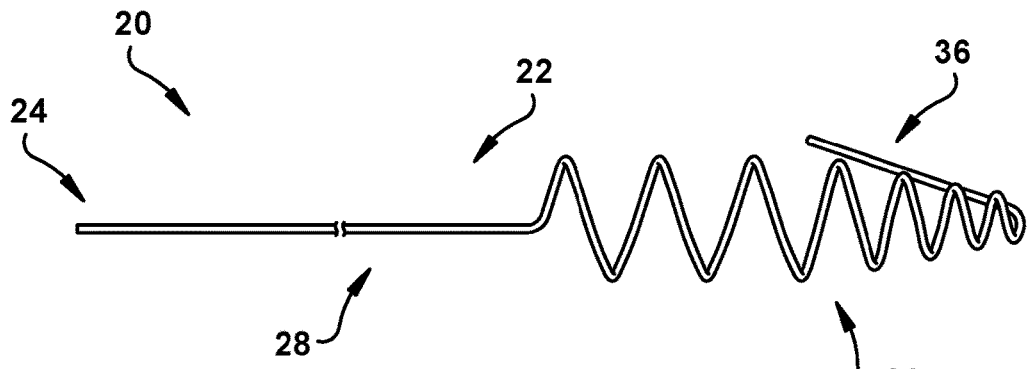
FIG. 2A is a schematic illustration of a neural electrode constructed in accordance with one aspect of the present disclosure.
Figure 2B:
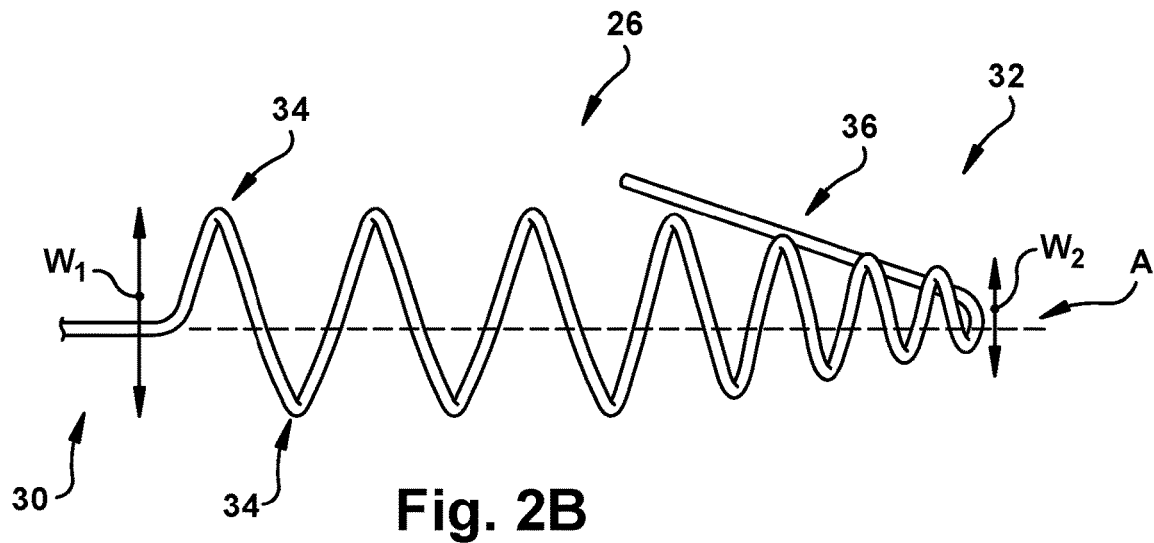
FIG. 2B is a schematic illustration showing a magnified view of a distal anchoring end of the neural electrode in FIG. 2A.

The distal anchoring end 26 of the neural electrode 20 can be configured for implantation within a target nerve or target nerve structure, and have a spiral or helical shape to prevent pullout of the neural electrode from the target nerve or target nerve structure. In one example, the distal anchoring end 26 can be configured for implantation within a fascicle 12 comprising a target nerve or target nerve structure, and have a spiral or helical shape to prevent pullout of the neural electrode 20 from the fascicle. The distal anchoring end 26 can have a first proximal end 30 with a first width $W_1$ that tapers to a second distal end 32 with a second width $W_2$ that is less than the first width $W_1$. The distal anchoring end 26 can comprise a three-dimensional curve with one or more turns 34 about an axis A. The distal anchoring end 26 can comprise two, three, or four or more turns 34. As shown in FIG. 2B, the distal anchoring end 26 can comprise a helix having twelve turns 34. The distal anchoring end 26 can further comprise an extension portion that extends tangential to (FIG. 2B), or substantially parallel with (FIG. 3), the axis A. The extension portion 36 can extend inside (FIG. 3) or outside (FIG. 2B) of the turns 34 comprising the distal anchoring end 26.

In another aspect, all or only a portion of the microwire body 22 can include an insulation material coated thereon and, optionally, one or more biocompatible agents adsorbed on the insulation material. In one example, only the proximal end 24 of the microwire body 22 can include an insulation material coated thereon. In another example, only the proximal end 24 and the middle portion 28 can include an insulation material coated thereon. In yet another example, the distal anchoring end 26 is free of any insulation material. In yet another example, the distal anchoring end 26 and the middle portion 28 do not include an insulation material coated thereon.

Figure 3:
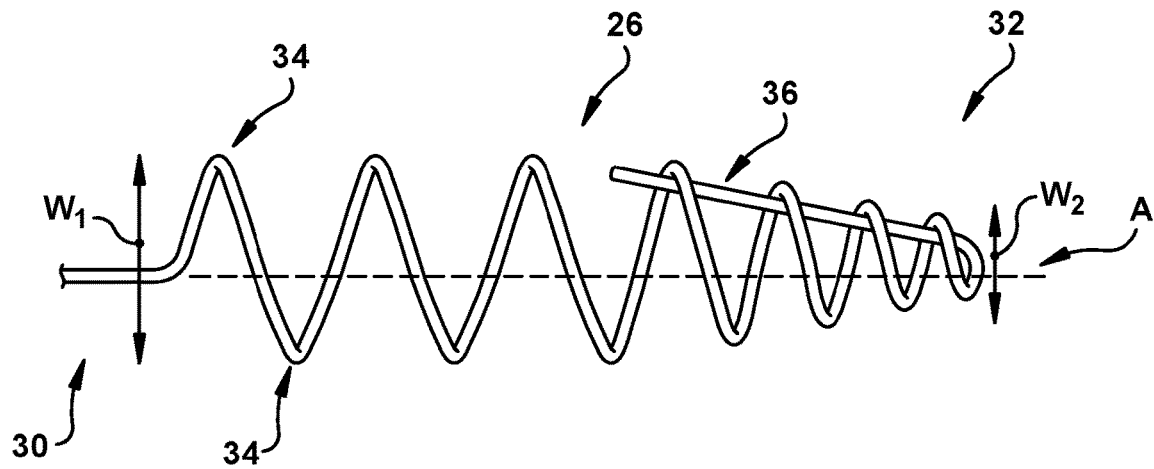
FIG. 3 is a schematic illustration of a neural electrode constructed in accordance with another aspect of the present disclosure.

It will be appreciated that the distal anchoring end 26 of the neural electrode 20 can have a configuration other than spiral-shaped so long as the distal anchoring end is still sized and dimensioned so as to prevent pullout of the neural electrode from a target nerve or target nerve structure. For example, only a portion of the distal anchoring end 26 may have a true spiral-shaped configuration (as shown in FIGS. 2A-B or FIG. 3, for instance) while the remaining portion of the distal anchoring end is somewhat coiled, but not a coil per se. Alternatively, the distal anchoring end 26 may not have a spiral-shaped configuration at all. Rather, the distal anchoring end 26 can comprise a knot or knot-like structure (e.g., a hitch) that is sized and dimensioned to prevent pullout of the neural electrode from a target nerve or target nerve structure. As discussed in more detail below, it will also be appreciated that regardless of the configuration of the distal anchoring end 26, the distal anchoring end can be sized and dimensioned for complete or partial implantation into a fascicle (e.g., the perineum) of a target nerve or target nerve structure.

Figure 4:
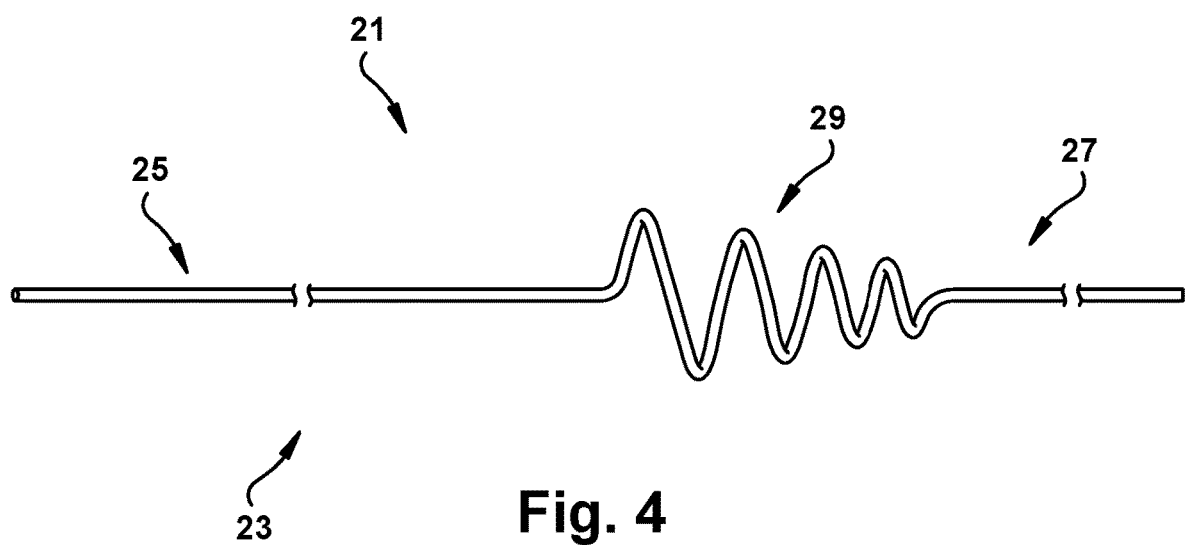
FIG. 4 is a schematic illustration of a neural electrode constructed in accordance with another aspect of the present disclosure.

Another aspect of the present disclosure is illustrated in FIG. 4. As shown in FIG. 4, an intrafascicular neural electrode 21 can comprise a microwire body 23 having a proximal end 25, a distal end 27, and a middle anchoring portion 29 extending between the proximal end and the distal end. At least a portion of the distal end 27 and/or the middle anchoring portion 29 can substantially match the mechanical and biological properties of a target nerve. In some instances, the middle anchoring portion 29 can have a spiral shape and the distal end 27 can have a straight, non-spiral shape. The spiral-shaped middle anchoring portion 29 can have four turns 34; however, it will be appreciated that a fewer or greater number of turns may form the spiral-shaped middle anchoring portion. Although the turns 34 comprising the middle anchoring portion 29 decrease in diameter from the proximal end 25 to the distal end 27, it will be appreciated that the reverse is possible, and that the diameter of each turn may be equal to the diameter of the other turns. As discussed in more detail below, the distal end 27 is configured for implantation within a fascicle while the middle anchoring portion 29 serves to secure intrafascicular neural electrode 21 once implanted and prevent pullout thereof.

In some instances, all or only a portion of the microwire body 23 can include an insulation material coated thereon and, optionally, one or more biocompatible agents adsorbed on the insulation material. In one example, only the proximal end 25 of the microwire body 23 can include an insulation material coated thereon. In another example, only the proximal end 25 and the middle anchoring portion 29 can include an insulation material coated thereon. In yet another example, the distal end 27 is free of any insulation material. In yet another example, the distal end 27 and the middle anchoring portion 29 do not include an insulation material coated thereon.

In another aspect, the neural electrode 20 (e.g., the microwire body 22) can have a flexural rigidity that is equal to, or about equal to, the flexural rigidity of a target nerve or target nerve structure in which the neural electrode is implanted. In one example, the neural electrode 20 (e.g., the microwire body 22) can have a flexural rigidity of about $10^{-12}$ N-m$^2$ to about $10^{-17}$ N-m$^2$. In another example, the neural electrode 20 (e.g., the microwire body 22) can be made of a carbon nanotube wire (e.g., less than 10 micron diameter) and have a flexural rigidity of about (or equal to) $10^{-15}$ N-m$^2$.

A significant problem with current nerve interfaces, such as intrafascicular implants is that the duration of the implant is very limited. This is due to a lack of mechanical compatibility with the nerve tissue in which the implant is placed. Mechanical compatibility is generally measured by the flexibility of the implant (e.g., a wire) in a target nerve or target nerve structure. The metric for wire flexibility is called flexural rigidity, and has not been addressed for any of these conventional nerve interfaces (e.g., intrafascicular interfaces). Based on the definition of flexural rigidity (provided above), the flexural rigidity of current neural interfaces was calculated and is presented in Table 1.

insulation materials that is/are biocompatible with perineurium cells or other fibrous tissue. Further, the insulation material(s) can include one or combination of materials that maintain the nerve-blood barrier. In one example, the entire microwire body 22, except for a portion thereof that is implanted within a fascicle 12 (e.g., the distal anchoring end 26), can be coated with one or a combination of insulation materials. Thus, in another example, the non-insulated portion of the microwire body 22 can be implanted (e.g., entirely implanted) within a fascicle 12, which may or may not include the entire distal anchoring end 26. As discussed more below, the insulated portion of the microwire body 22 should directly contact the perineurium 16 when the microwire body is implanted within a fascicle 12. In some instances, the insulation material can be one of parylene, silicone or plasma-deposited amorphous carbon. In one example, the insulation material can comprise a 2-micron thick layer of plasma-modified silicone. At least one biocompatible agent can be adsorbed to an outer surface of the insulation material. The biocompatible agent can comprise any biological or organic molecule that improves the biocompatibility of the neural electrode 20 (e.g., improves biocompatability with perineurium cells). In some instances, the biocompatible agent is a biological or organic molecule (e.g., collagen, fibronectin) produced by one or more cells associated with, or comprising, the biological medium surrounding an implanted neural electrode 20. Where a neural electrode 20 is to be implanted in a fascicle 12, for example, collagen and/or fibronectin and/or another other similar molecule can be adsorbed onto the insulation material. This is advantageous because the endogenous cells surrounding fascicles 12 naturally produce collagen. In another example,

TABLE 1

Flexural Rigidity of Conventional Neural Interfaces

| Structure | E (N/m$^2$) | Dimensions | I$_x$ (m$^4$) | I$_y$ (m$^4$) | FR$_{max}$ (N-m$^2$) |
|---|---|---|---|---|---|
| tf-LIFE | 8.3 GPa | b = 220 μm/h = 10 μm | 18.33e-21 | 8.87e-18 | 73.62e-9 |
| TIME | 8.3 GPa | b = 280 μm/h = 5.5 μm | 3.88e-21 | 10.06e-18 | 83.50e-9 |
| Pt-10% Ir Wire | 202.3 GPa | 10 μm diameter | 490.87e-24 | 490.87e-24 | 99.30e-12 |
| Parylene-C | 2.8 GPa | r$_2$ = 7 μm/r$_1$ = 5 μm | 1.39e-21 | 1.39e-21 | 3.89e-12 |
| Silicone | .001-.05 GPa | r$_2$ = 7 μm/r$_1$ = 5 μm | 1.39e-21 | 1.39e-21 | 69.5e-15 |
| Carbon Nanotubes | 0.2 GPa | 5 × 5 μm$^2$ sq. block | 5e-24 | 5e-24 | 1e-15 |
| Carbon Nanotube Wires | 0.2 GPa | r = 5 μm, t = 180 nm | 70.69e-24 | 70.69e-24 | 14.14e-15 |
| Rod Photoreceptors | | 60 μm long, 6.5 μm in diameter | | | 2.77e-16 |
| Nerves | 580 KPa | Variable length, diameter between 0.2 and 30 μm | 0.6e-21 | 1.3e-21 | 7.5e-16 |

The calculations show that current prostheses, such as the TIME and LIFE have flexural rigidity values ($10^{-9}$) seven orders of magnitude greater than endogenous, string-like structures, such as the photoreceptors rods or nerves ($10^{-16}$). By contrast, a neural electrode 20, 90 according to the present disclosure, which is made of a carbon nanotube wire, for example, has a flexural rigidity value of $10^{-15}$. By having a flexural rigidity value that is close or identical in magnitude to that of the biological medium surrounding an implanted neural electrode, the foreign body reaction (inflammation) is advantageously minimized while compliance with the target nerve or target nerve structure is maximized, thereby enabling chronic implantation of the neural electrode 20, 90.

In another aspect, all or only a portion of the microwire body 22 can be coated with one or a combination of where a neural electrode 20, 90 is to be implanted in the brain of subject, one or a combination of molecules, such as proteins (e.g., laminin), proteoglycans, and polysaccharides (e.g., hyaluronic acid) can be adsorbed onto the insulation material.

In one example, an intrafascicular neural electrode 20 can comprise a microwire body 22 coated with an insulation material and biocompatible agent comprising silicone with collagen adsorption. One risk with neural implants that cross the perineurium 16 is the lack of adherence with the perineurium cells to ensure that perineurium will form a seal around the implant. To further reduce the risk of inflammation around the neural electrode 20, the microwire body 22 can include silicone insulation with collagen, which can advantageously increase cell adhesion as well as help in the formation of a tight seal between the microwire body 22 and the perineurium. In such instances, the microwire body 22 can be made of carbon nanotubes, which are compatible with neural tissue, promote the growth of neurons, and improve neural signal recordings.

It will be appreciated that the neural electrode 20 can additionally or optionally be doped with at least one chemical or pharmaceutical agent that is selectively released therefrom (e.g., by application of electrical energy or diffusion). Such chemical or pharmaceutical agents can be any agent that modulates cellular activity, such as inhibiting one or more cellular activity or inducing one or more cellular activity. Such chemical or pharmaceutical agents should be selected for compatibility with the component materials of the neural electrode 20, and should be present in amounts effective to modulate cellular activity.

Implantation Methods

Figure 5:
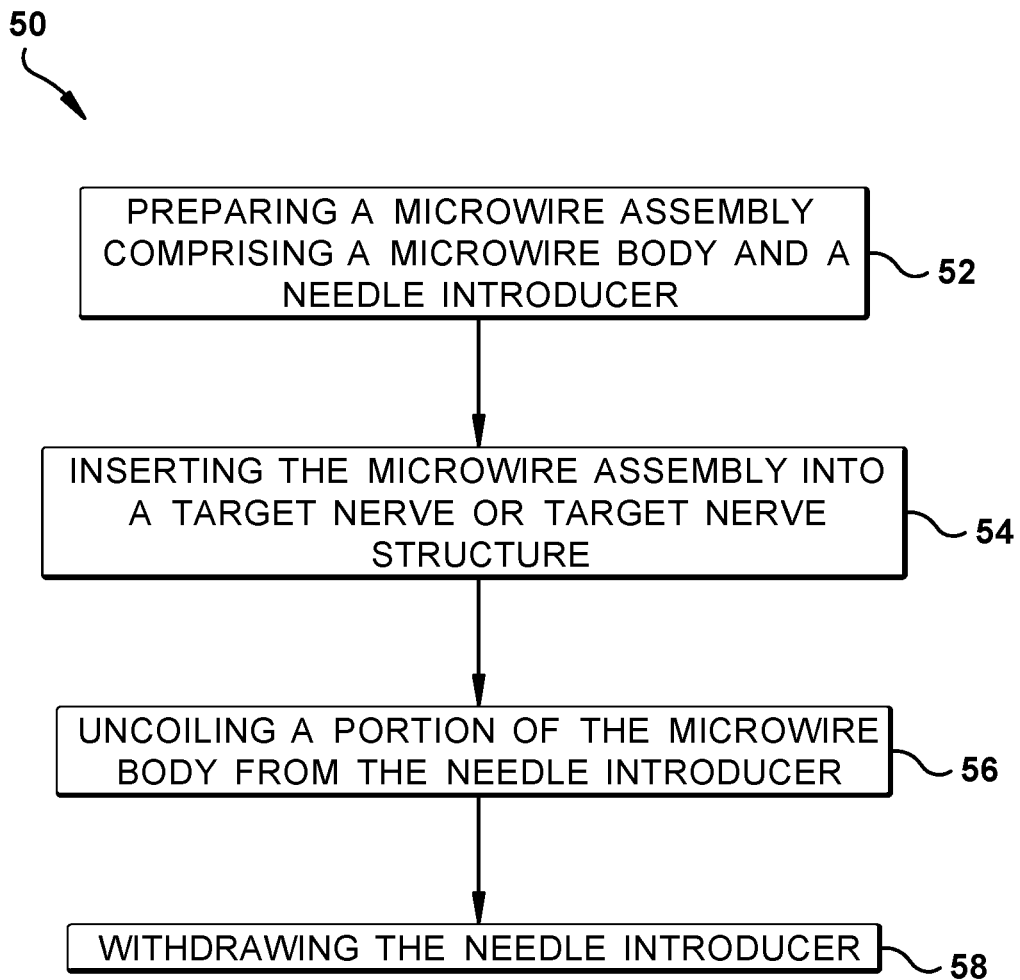
FIG. 5 is a process flow diagram illustrating a method for implanting a neural electrode in a target nerve or target nerve structure according to another aspect of the present disclosure.

Another aspect of the present disclosure can include a method 50 (FIG. 5) for implanting a neural electrode 20 in a target nerve or target nerve structure of a subject. Although the method 50 will be described below in terms of implanting a neural electrode 20 in a fascicle 12 comprising a target nerve, it will be appreciated that the method can also be used to implant a neural electrode in a different target nerve or target nerve structure, such as nervous tissue comprising the CNS (e.g., the brain or spinal cord). The method 50, as described below, overcomes the difficulties and limitations associated with intrafascicular neural electrode implantation where, for example, LIFE implantation requires threading such implants through a particular peripheral nerve and then tacking the implant using sutures at both the proximal and distal ends, which causes significant damage to the nerve. Further, where wire-like implants (such as LIFEs) are used, the relatively low flexural rigidity of such implants makes insertion of the implants through the perineum essentially impossible.

Figure 6:
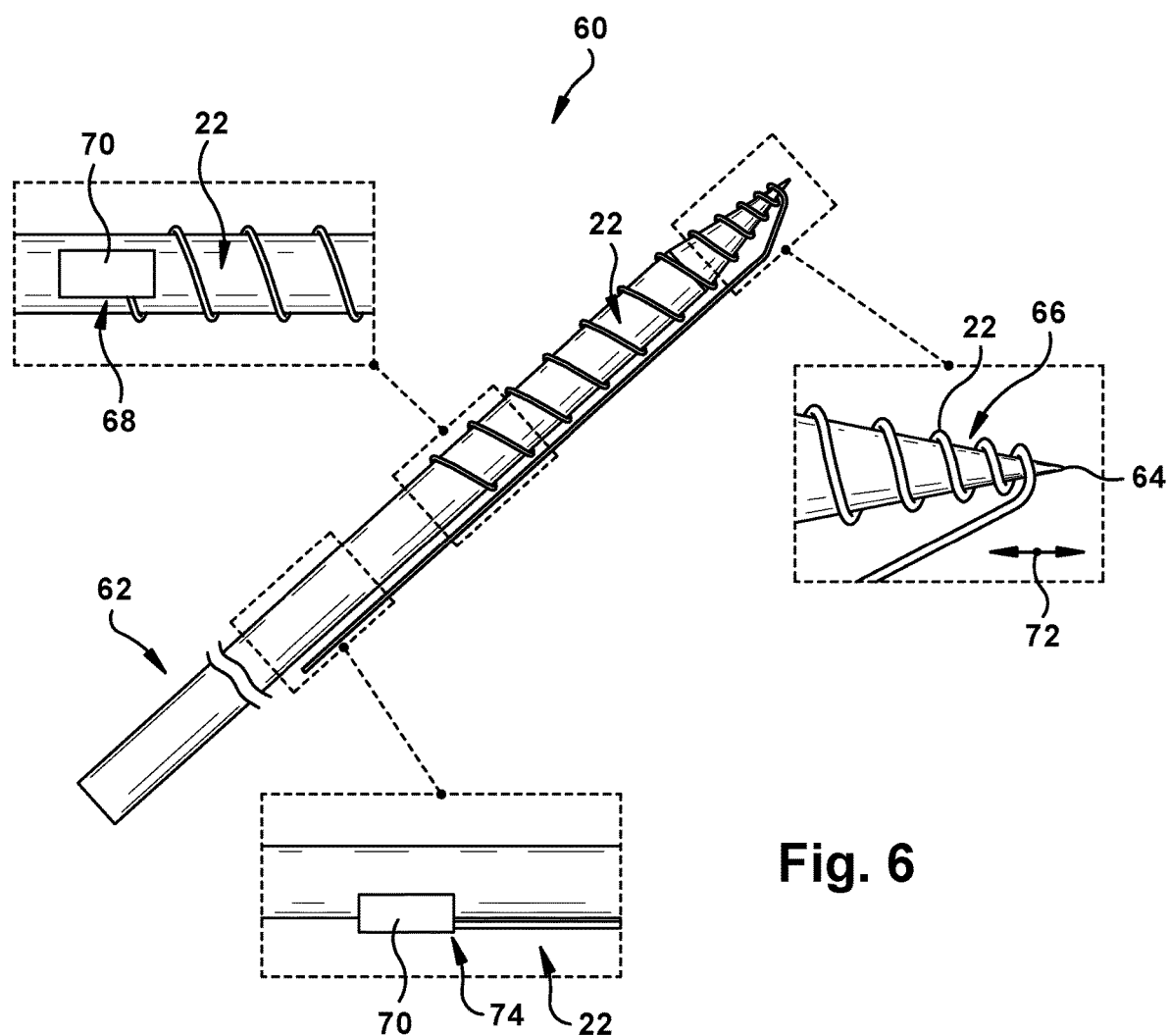
FIG. 6 is a schematic illustration showing preparation of a microwire assembly according to the method of FIG. 5.

To overcome these obstacles, Step 52 of the method 50 can include preparing a microwire assembly 60 (FIG. 6). As shown in FIG. 6, a microwire body 22 can be coiled around a needle introducer 62. The needle introducer 62 can comprise a microneurography needle having, for example, an atraumatic distal tip 64 (e.g., about 3 micron diameter rounded tip) and a conical distal end portion 66 with a tapering angle of about 5-10 degrees. The needle introducer 62 can have a diameter of about 75 microns to about 200 microns or more. In one example, the needle introducer 62 can comprise a tungsten microneurography needle that is commercially available from FHC Inc. (Bowdoin, Me.) and has a 5-10 taper angle and a 100 micron diameter.

To prepare the microwire assembly 60, a first end 68 of the microwire body 22 is secured to a portion of the needle introducer 62 (e.g., using a piece of tape 70). The microwire body 22 can then be wound around the needle introducer 62 towards the distal tip 64 until it reaches a point just proximal to the distal tip (e.g., about 20-50 microns before the distal tip). Thus, the microwire body 22 does not cover a portion 72 of the needle introducer 62. The microwire body 22 is not wound around this portion 72 so that it does not interfere with the ability of the distal tip 64 to pierce the target nerve. Next, a second end 74 of the microwire body 22 can be pulled in a proximal direction so that it can be secured to the needle introducer 62 (e.g., via a piece of tape 70).

Figure 7:
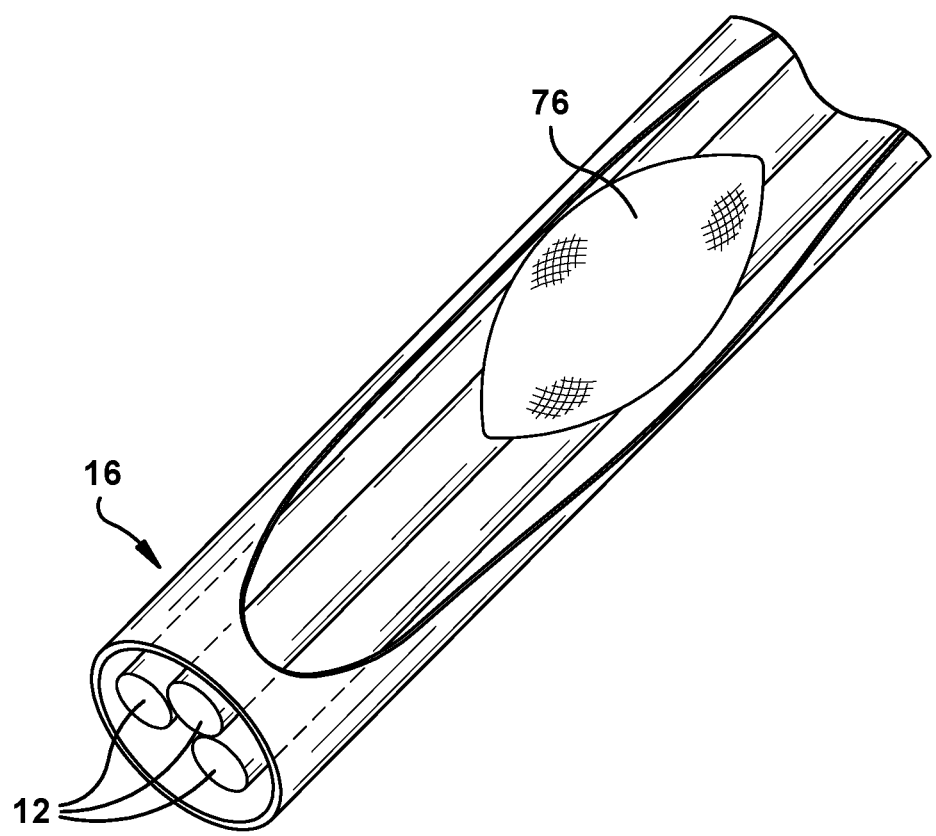
FIG. 7 is a schematic illustration showing surgical preparation of a target nerve comprising a plurality of fascicles prior to insertion of the microwire assembly.

If it has not been done so already, the target nerve can be surgically prepared to receive the microwire assembly 60. To do so, an incision in the epineurium 14 can be made as shown in FIG. 7. Making the incision exposes the fascicles 12 comprising the target nerve. An amount of collagenase 76 can be contacted with the exposed portion of the nerve after the incision is made. The addition of collagenase 76 helps to expose the fascicles 12 as the fascicles are embedded within collagen.

Figure 8:
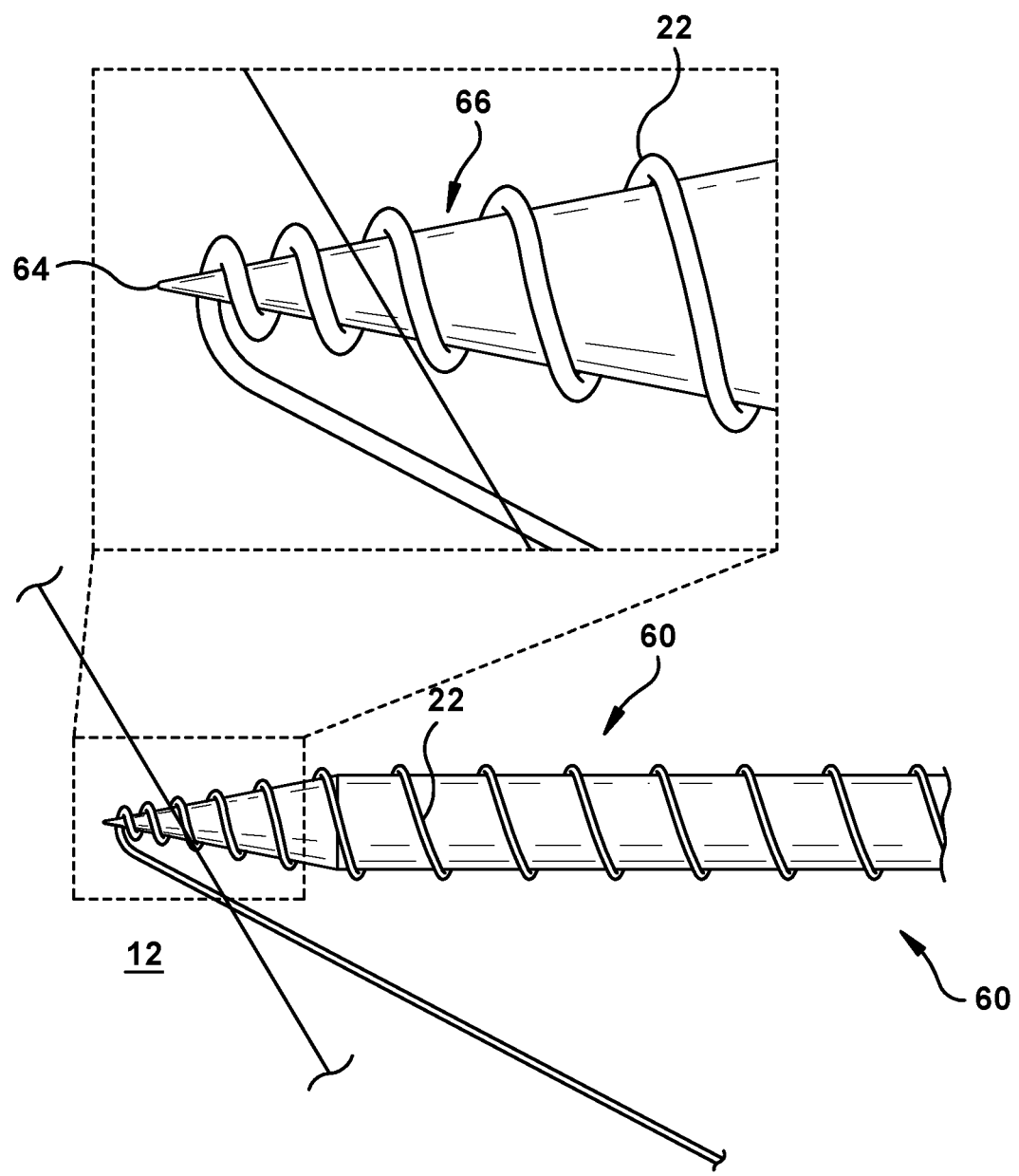
FIG. 8 is a schematic illustration showing insertion of the microwire assembly into one of the fascicles in FIG. 7.

At Step 54, the microwire assembly 60 can be inserted into a fascicle 12. To do so, the microwire assembly 60 can be advanced through the perineurium 16 into the fascicle 12 such that at least a portion of the distal end portion 66 of the needle introducer 62, which includes the microwire body 22 coiled thereabout, is disposed therein (FIG. 8). Advantageously, use of the needle introducer 62 permits quick and efficient insertion of the microwire body 22 into the fascicle 12. As discussed above, this is essentially impossible using only a wire-like implant itself (e.g., a LIFE) due to the relatively low flexural rigidity of such implants. The needle introducer 62 thus serves as a rigid guide that enables efficient insertion of the microwire body 22 that would otherwise not be possible given the low flexural rigidity of the neural electrode 20.

Figure 9:
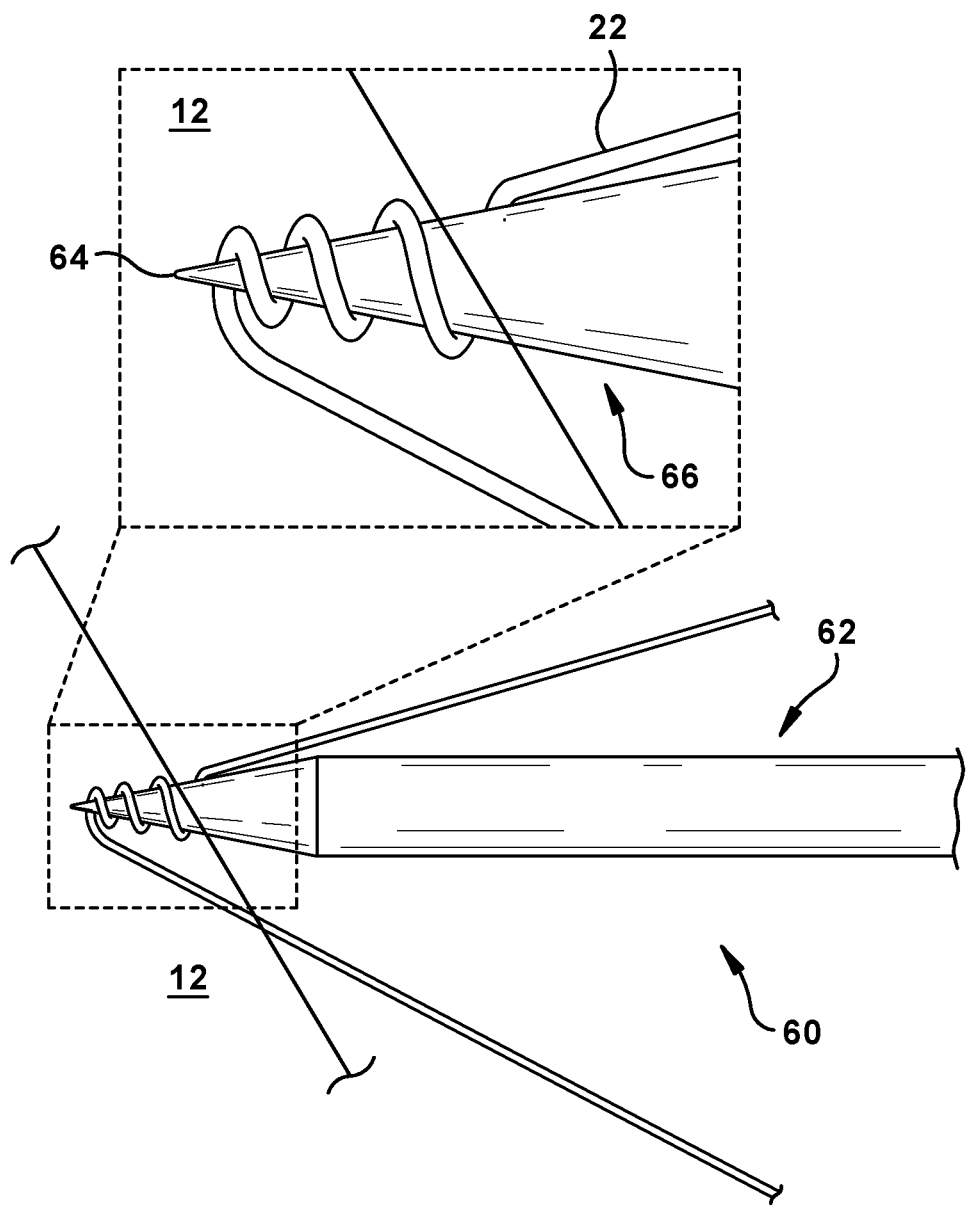
FIG. 9 is a schematic illustration showing uncoiling of a microwire body from the microwire assembly in FIG. 8.
Figure 10A:
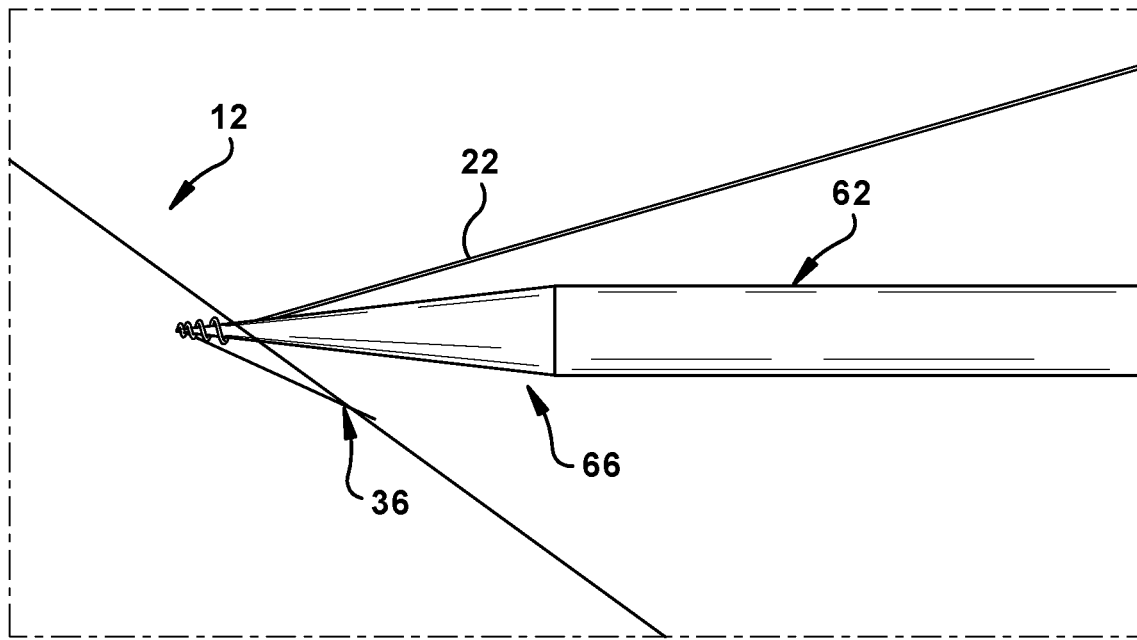
FIGS. 10A-B are schematic illustrations showing insertion of a distal anchoring end of the microwire body in FIG. 9 into the fascicle.
Figure 10B:
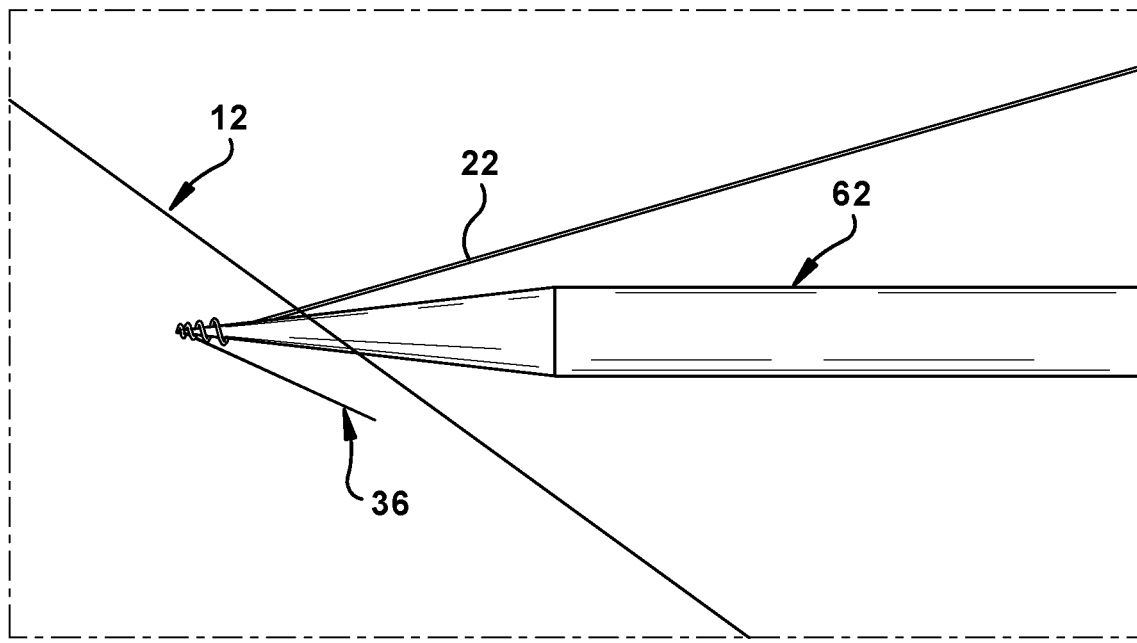

Next, at Step 56, the portion of the microwire body 22 that is exposed outside of the target nerve can be unwound from the needle introducer 62 while the portion of the microwire body inside the fascicle 12 remains wound around the distal end portion 66 of the needle introducer (FIG. 9). After uncoiling a portion of the microwire body 22 from the needle introducer 62, the unwound portion of the microwire body (that extends from inside of the fascicle 12) can be cut to form the extension portion 36 (FIG. 10A). After doing so, the needle introducer 62 is further advanced into the fascicle 12 until the extension portion 36 is completely embedded or located within the fascicle (FIG. 10B).

Figure 11:
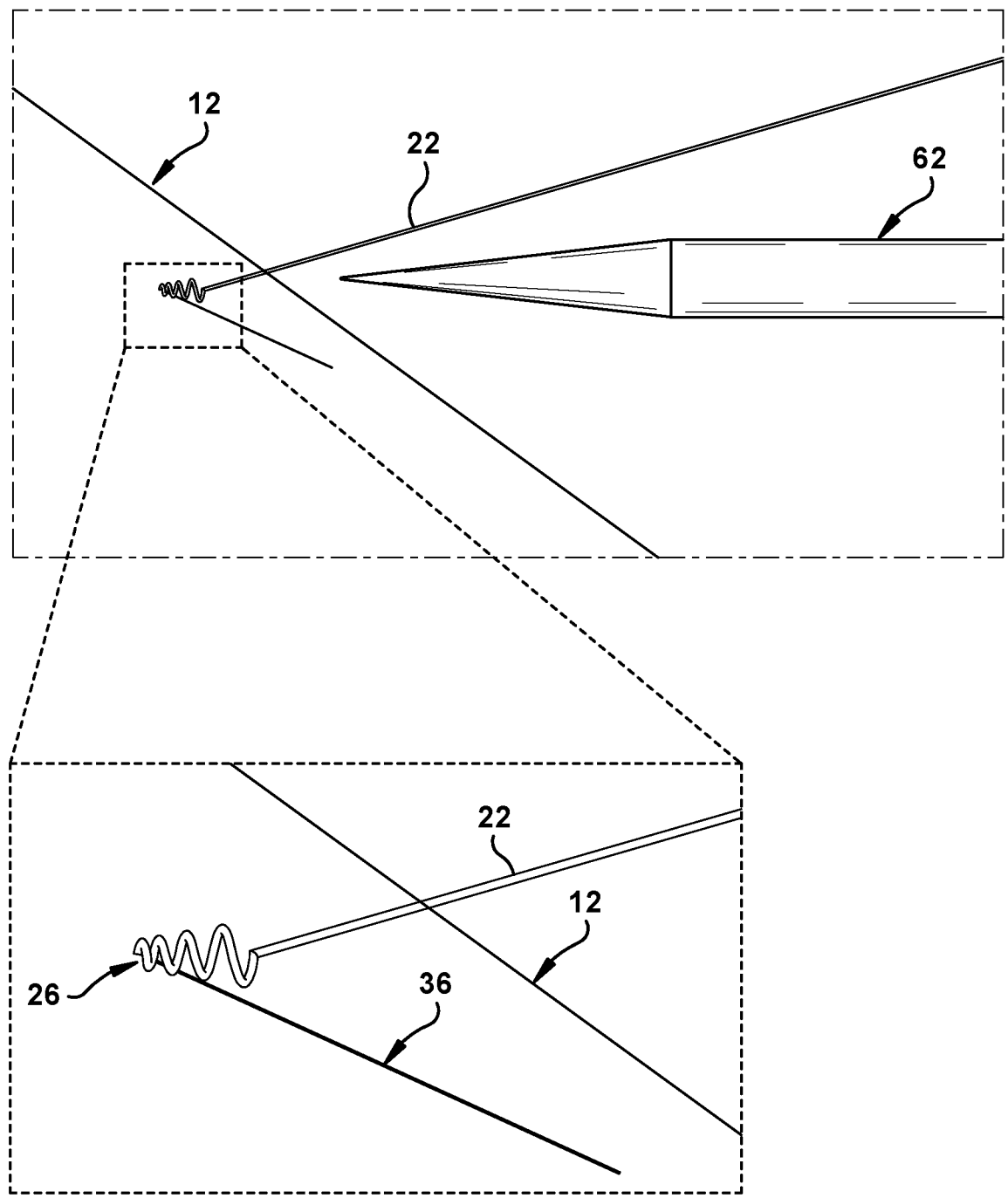
FIG. 11 is a schematic illustration showing withdrawal of an introducer needle from the microwire body in FIGS. 10A-B.
Figure 12:
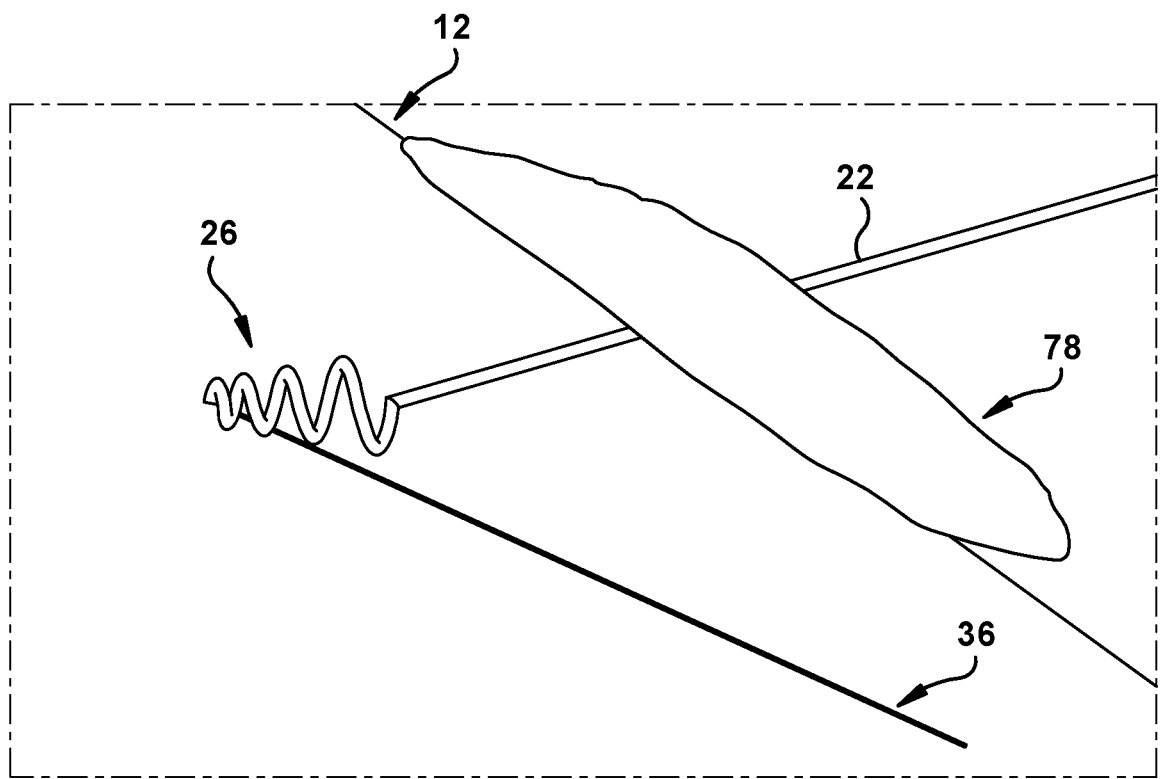
FIG. 12 is a schematic illustration showing the microwire body, and in particular the anchoring end thereof, securely implanted in the fascicle.
Figure 15:
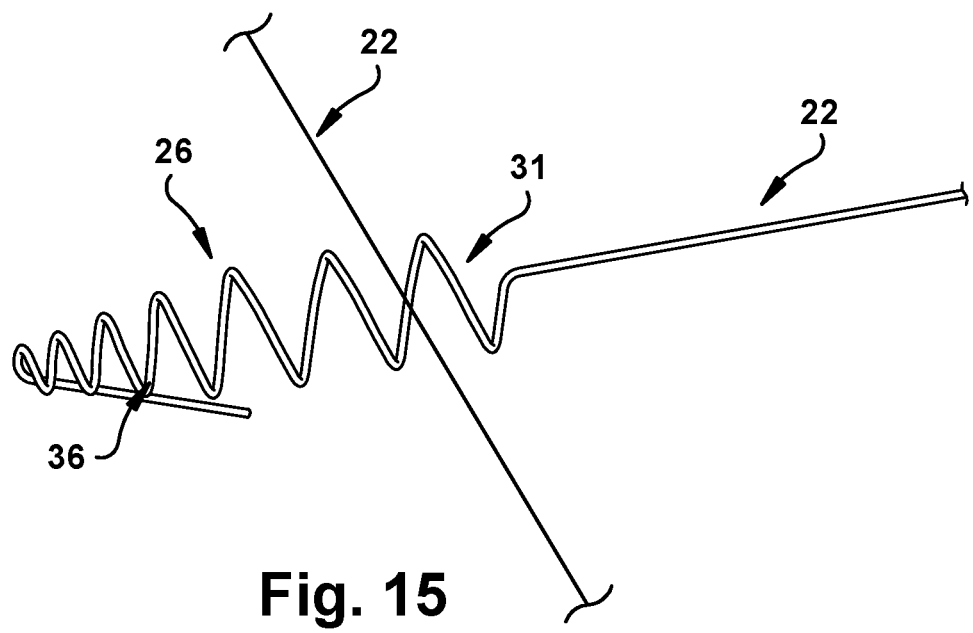
FIG. 15 is a schematic illustration showing the microwire body, and in particular the anchoring end thereof, partly implanted in a fascicle.

At Step 58, the needle introducer 62 can be withdrawn by holding the portion of the microwire body 22 that is not embedded within the fascicle 12 (FIG. 11). In doing so, only the microwire body 22 (e.g., the distal anchoring end 26) remains within the fascicle 12. For example, the entire distal anchoring end 26 can remain embedded or located within the fascicle 12. Alternatively, as shown in FIG. 15, only a portion of the distal anchoring end 26 remains implanted within the fascicle 12 (e.g., within the perineum) while a another portion 31 of the distal anchoring end remains outside of the fascicle (e.g., outside of the perineum). Advantageously, the spiral or helical-shaped distal anchoring end 26 that remains embedded within the fascicle 12 reduces or eliminates pullout of the neural electrode 20 from the fascicle. Additionally, the remaining distal anchoring end 26 advantageously obviates the need for placement of sutures to secure the neural electrode 20. Advantageously, the presence of a biocompatible agent (or agents), such as collagen on the microwire body 22 promotes attachment to, and integration with, the native collagen of the fascicle 12, thereby also serving to secure the neural electrode 20 without the need for placement of sutures to secure the neural electrode. To further secure the microwire body 22 to the fascicle 12, a fibrin sealant 78 (or other biocompatible material) can be deposited over the microwire body as shown in FIG. 12. If it has not been done so already, the proximal end 24 of the microwire body 22 can be placed into electrical communication with electronics (not shown) to permit recording, measuring and/or stimulating nerve activity in the fascicle 12.

It should be appreciated that, for certain implantation areas, the microwire body 22 can be configured for attachment to nearby tissue using one or more anchoring materials (not shown). For implant areas that experience a relatively high degree of motion (e.g., joints in the legs and arms), for instance, all or only a portion of the insulated portion of the microwire body 22 can be attached to an anchoring material (e.g., Dacron mesh) (e.g., by looping the microwire body on or within the anchoring material). After the insulated portion of the microwire body 22 has been attached to the anchoring material, the anchoring material can be sutured to nearby tissue. Advantageously, use of the anchoring material serves as an additional anchor point to help prevent the microwire body 22 from being pulled out of the nerve during motion.

Figure 13:
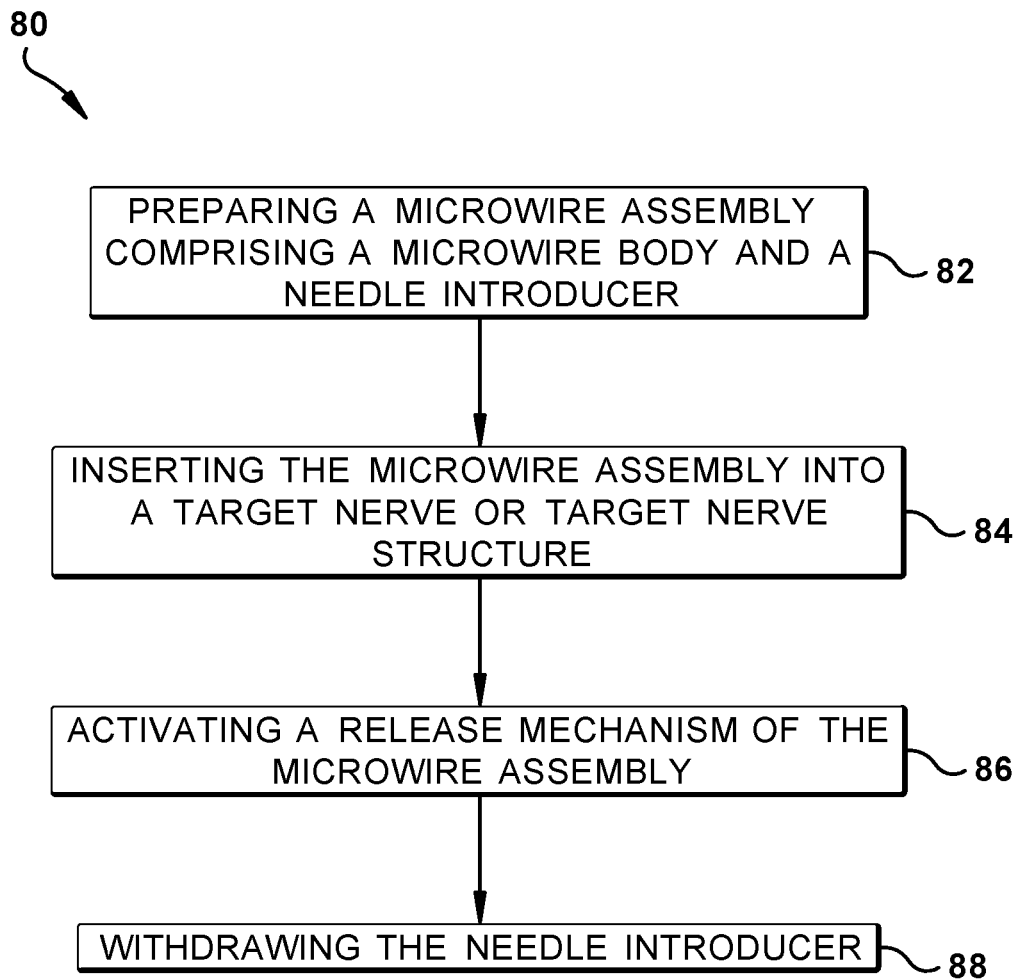
FIG. 13 is a process flow diagram illustrating another method for implanting a neural electrode in a target nerve or target nerve structure according to an aspect of the present disclosure.

Another method 80 for implanting a neural electrode 90 (FIG. 14) in a target nerve or target nerve structure of a subject is shown in FIG. 13. Although the method 80 will be described below in terms of implanting a neural electrode 90 in a fascicle 12 comprising a target nerve or target nerve structure, it will be appreciated that the method can also be used to implant a neural electrode in other target nerves or target nerve structures, such as nervous tissue comprising the CNS (e.g., the brain or spinal cord). The method 80, as described below, overcomes the difficulties and limitations associated with intrafascicular neural electrode implantation where, for example, LIFE implantation requires threading such implants through a particular peripheral nerve and then tacking the implant using sutures at both the proximal and distal ends, which causes significant damage to the nerve. Further, where wire-like implants (such as LIFEs) are used, the relatively low flexural rigidity of such implants makes insertion of the implants through the perineum essentially impossible.

Figure 14:
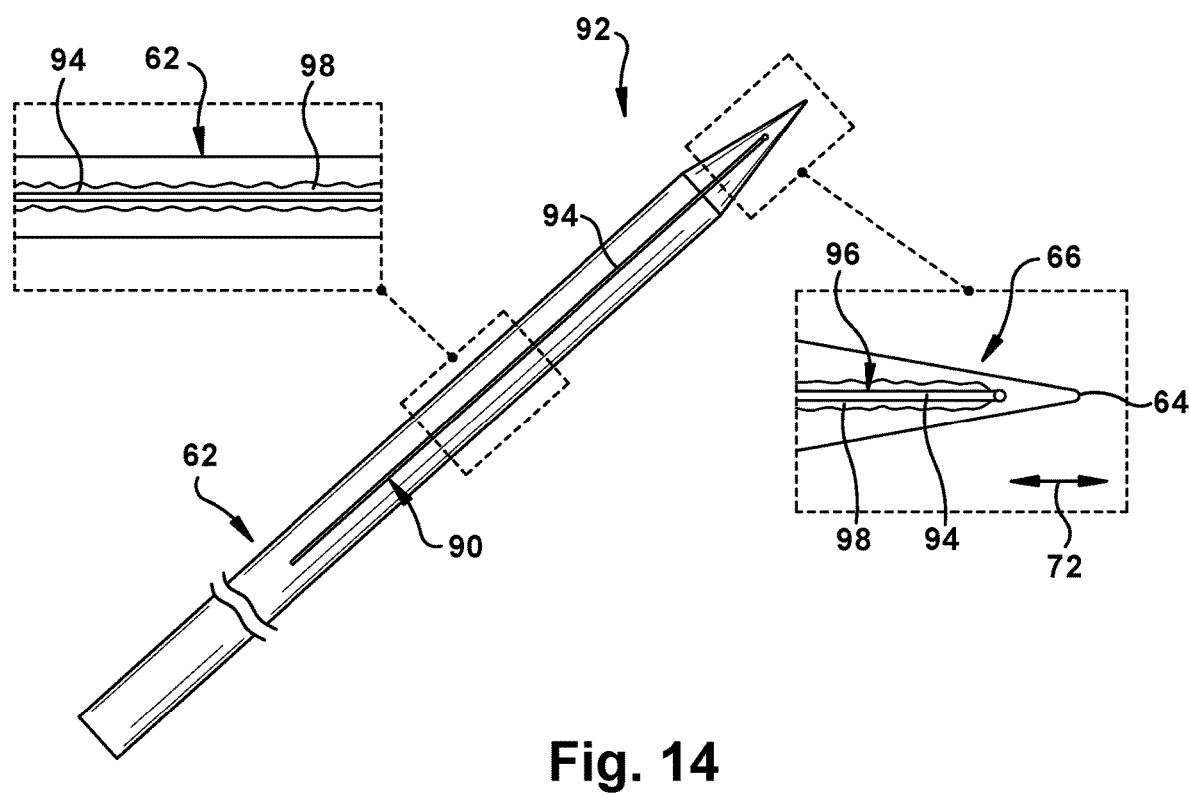
FIG. 14 is a schematic illustration of a microwire assembly constructed in accordance with another aspect of the present disclosure.

To overcome these obstacles, Step 82 of the method 80 can include preparing a microwire assembly 92 (FIG. 14). The microwire assembly 92 can comprise a microwire body 94 that is releasably coupled or attached to a needle introducer 62. The microwire body 94 can have a linear or straight wire-like shape and include a distal end portion 96. The microwire body 94 can have a diameter that is equal to, or about equal to, the diameter of the microwire body 22 described above. Additionally, the microwire body 94 can be made of the same or different material(s) as described for the microwire body 22 above. The microwire body 94 can be coupled or attached to the needle introducer 62 so that the distal end portion 96 of the microwire does not span or overlap the distal tip 64 of the needle introducer, thereby leaving a portion 72 that is not covered by the microwire body.

The microwire body 94 can be releasably coupled to the needle introducer 62 via a selective release mechanism. The selective release mechanism enables the microwire body 94 to be temporarily attached to the needle introducer 62 during implantation (e.g., insertion) of the neural electrode 90 into a target nerve. Then, when withdrawal of the needle introducer 62 is appropriate, an operator (e.g., a physician or surgeon) can selectively activate the release mechanism to physically detach and separate the microwire body 94 from the needle introducer. Depending upon the particular release mechanism, activation can occur by tactile, chemical, mechanical, electrical and/or optical means. In one example, the microwire body 94 can be releasably coupled to all or only a portion of the needle introducer 62 via a biocompatible and dissolvable or degradable substance 98 (FIG. 14), such as a sugar (e.g., sucrose) or other biocompatible adhesive. In this case, the microwire body 94 can be released from the needle introducer 62 upon application of a solvent (e.g., sterile saline and/or a bodily fluid) to the substance 98. Other non-limiting examples of release mechanisms can include clips, fasteners, polymers configured for selective degradation (e.g., upon exposure to electrical and/or optical energy), and magnetic components. Still further, the needle introducer 62 can include a channel (not shown) and/or groove (not shown) that is sized and dimensioned to accommodate the microwire body 94 so that the microwire body is securely seated within the channel and/or groove during implantation.

If it has not been done so already, the target nerve can be surgically prepared to receive the microwire assembly 92 (as discussed above).

At Step 84, the microwire assembly 92 can be inserted into a target nerve or target nerve structure, such as a fascicle 12. To do so, the microwire assembly 92 can be advanced through the perineurium 16 into the fascicle 12 such that at least a portion of the distal end portion 96 of the needle introducer 62, which includes the microwire body 94 disposed thereon, is located therein. Advantageously, use of the needle introducer 62 permits quick and efficient insertion of the microwire body 94 into the fascicle 12. As discussed above, this is essentially impossible using only a wire-like implant itself (e.g., a LIFE) due to the relatively low flexural rigidity of such implants. The needle introducer 62 thus serves as a rigid guide that enables efficient insertion of the microwire body 94 that would otherwise not be possible given the low flexural rigidity of the neural electrode 90.

Next, at Step 86, the release mechanism can be selectively activated so that at least the distal end portion 96 of the microwire body 94 is physically detached, and separated from, the needle introducer 62. In some instances, selective activation of the release mechanism causes the entire microwire body 94 to be physically detached, and separated from, the needle introducer 62. In one example, where the microwire body 94 is releasably coupled to the needle introducer 62 by a compatible and dissolvable substance 98 (e.g., sucrose), a solvent (e.g., sterile saline) can be contacted with the portion of the microwire assembly 92 that is not embedded within the fascicle 12 to dissolve the substance 98 and cause the microwire body 94 to physically detach from the needle introducer 62. At about the same time, the distal end portion 96 of the microwire body 94 (which is embedded in the target nerve) can be physically detached from the needle introducer 62 upon dissolution of the substance 98 therebetween (e.g., by the presence of physiological fluid(s) within the target nerve). As discussed above, it will be appreciated that different actions can be taken to cause physical release of the microwire body 94 from the needle introducer 62 depending upon the particular type and/or construction of the release mechanism.

At Step 88, the needle introducer 62 can be withdrawn so that only the microwire body 94, and in particular the distal end portion 96, remains within the fascicle 12. For example, the entire distal end portion 96 can remain embedded or located within the fascicle 12. Advantageously, the presence of a biocompatible agent (or agents), such as collagen on the microwire body 94 promotes attachment to, and integration with, the native collagen of the fascicle 12, thereby serving to secure the neural electrode 90 without the need for placement of sutures to secure the neural electrode. To further secure the microwire body 94 to the fascicle 12, a fibrin sealant 78 (or other biocompatible material) can be deposited over the microwire body (as described above). If it has not been done so already, a proximal end of the microwire body 94 can be placed into electrical communication with electronics (not shown) to permit recording, measuring and/or stimulating nerve activity in the fascicle 12.

Applications

Another aspect of the present disclosure can include methods of treating a condition or disorder associated with impaired neural function in a patient comprising the neural electrode 20, 90 of the present disclosure. Examples of conditions or disorders associated with impaired neural function can include, but are not limited to, impairment or loss of tactile sensation, impaired hearing, impaired vision, impaired motor control, impaired bladder control, Parkinson's disease, paraplegia or tetraplegia, amyotrophic lateral sclerosis, loss of bowel control, erectile dysfunction, loss of cognitive function, gastroparesis, irregular heartbeat and pain.

Thus, the neural electrode 20, 90 of the present disclosure is useful for providing renewed neural function or sensation to a patient who has previously lost neural function or sensation, for example, in the case of an amputation (e.g., in patients with upper-arm amputation since muscle activity recording is not possible in such patients and ENG from remaining nerves is the only option available in the PNS, or in patients with trans-humeral amputation who are missing crucial muscles and lower extremities). The neural electrode 20, 90 can provide sensory information to the patient by stimulating the sensory afferent nerves in order to relay information from one or more sensors mounted on a prosthesis to measure touch, temperature, force, position, orientation, and the like.

Another use of the neural electrode 20, 90 is to record the activity of motor neurons and use the recorded signal to drive the motors on a prosthesis. Yet another use would be combining the neural electrode 20, 90 with a separate sensor in a closed-loop system, wherein the separate sensor is used to measure a physiological variable such as, for example, end tidal carbon dioxide during respiration, and use that variable to trigger stimulation of the phrenic nerve via the neural electrode. In yet further applications, the neural electrode 20 can be implanted in the spinal cord or brain and, upon implantation, the neural electrode can be designed to release a pharmaceutical (e.g., a nerve growth factor) by any number of mechanisms known to one of skill in the art (e.g., by degradation of a slow release coating, or release of active agent upon electrical impulse supplied to the neural electrode).

Another aspect can include neuroprosthetic devices that comprise one or more of the neural electrodes 20, 90 of the present disclosure. This aspect broadly relates to any type of neuroprosthetic device that can be designed and used to replace or improve the function of an impaired nervous system or to augment the function of a non-impaired nervous system. Prosthetic devices that incorporate a system for sending and/or receiving electrical stimulus to neural cells are known generally in the art, and can be modified to work with the neural electrodes disclosed herein (e.g., cochlear implants, brain and brainstem implants (e.g., auditory, visual cortex (vision), motor (movement control), etc.), spinal and lumbar anterior root implants, implants that support function of the autonomous nervous system such as, for example, bladder control (sacral anterior root stimulator), and the like.

Sensory/motor prosthetics seek to establish an interface with neurons that provide limb movement and touch sensation (for example, an implant interfaced directly into the median nerve fibers for movement of, and recording of touch feedback in, an artificial limb). Several strategies exist that seek to achieve advanced control of neural prosthetics, in general. Direct chronic brain implants record neuronal signals from the motor cortex, while methods such as electroencephalography (EEG) and functional magnetic resonance imaging (fMRI) obtain motor commands non-invasively. The recorded signals are decoded into electrical signals, and input into assistive devices or motorized prosthetics. Traditional myoelectric prostheses utilize surface electromyography (EMG) signals from the remains of the amputated limb. For example, a patient may flex a shoulder muscle in order to generate EMG signals that may be used to send "bend elbow" command to the prosthesis. Targeted reinnervation is another surgical method which makes use of the patient's existing nerves and is aimed to provide an amputee with improved control over motorized prosthetic devices and to regain sensory feedback. Such motor neuroprosthetics find use in a wide variety of patient class, particularly those patients that have a disease or condition that impairs their ability to control muscle function, movement, and/or communicate (e.g., amputees).

Visual prosthetics are typically targeted and implanted within the visual cortex area of the brain, and can improve vision in patients having significantly impaired vision (but not total blindness). Auditory prosthetics, such as the cochlear implant and the auditory brain stem implant are surgically implanted into the cochlea, or brainstem, of patients who are deaf or severely hard of hearing. These implants are typically coupled with external components including a microphone, speech processor, and transmitter.

Pain relief prosthetics such as the Spinal Cord Stimulator or (Dorsal Column Stimulator) are used to treat chronic neurological pain. Typically, these implants are set near the dorsal surface of the spinal cord and an electric impulse generated by the device provides a "tingling" sensation that alters the perception of pain by the patient. In one type of implant arrangement, a pulse generator or RF receiver is implanted remotely (e.g., in the abdomen or buttocks) from the lead/electrode, which is connected to the generator by a wire harness. Cognitive prosthetics (e.g., hippocampal prosthesis) are aimed at restoring cognitive function by replacing circuits within the brain damaged by stroke, trauma or disease.

In one example, a neuroprosthetic device can incorporate a neural electrode 20, 90 of the present disclosure and be designed to induce or control a physiological response in a subject. Several non-limiting examples of devices that can incorporate the electrodes 20, 90 of the present disclosure can include stimulators, such as those for pacemakers for the vagus nerve (e.g., from Cyberonics, Inc., Houston, Tex.), for the pudendal nerve (bladder control), the ENTERRA Therapy subsystem (Medtronic, Inc., Minneapolis, Minn.) for stimulating the stomach muscles and treatment of gastroparesis, for deep brain stimulation (e.g., from Medtronic, Inc., Minneapolis, Minn.), and for pain relief (e.g., from Medtronic, Inc., Minneapolis, Minn.).

In another aspect, the present disclosure can include a method of augmenting neurological function in a person with normal neurological function comprising connecting to the PNS of the person at least one intrafascicular neural electrode 20, 90 of, and providing a stimulus via the intrafascicular neural electrode, wherein the stimulus elicits sensations in the sensory nerves of the PNS. In some instances, this method of augmenting neurological function in a person with normal neurological function can comprise connecting to the PNS of the person at least one intrafascicular neural electrode 20, 90, recording neural activity from the PNS, transmitting the recorded neural activity to an external device, wherein the transmission of recorded activity generates a response in the external device, and providing a return stimulus from the external device via the intrafascicular neural electrode, wherein the return stimulus elicits sensations in the sensory nerves of the PNS of the person.

Figure 17:
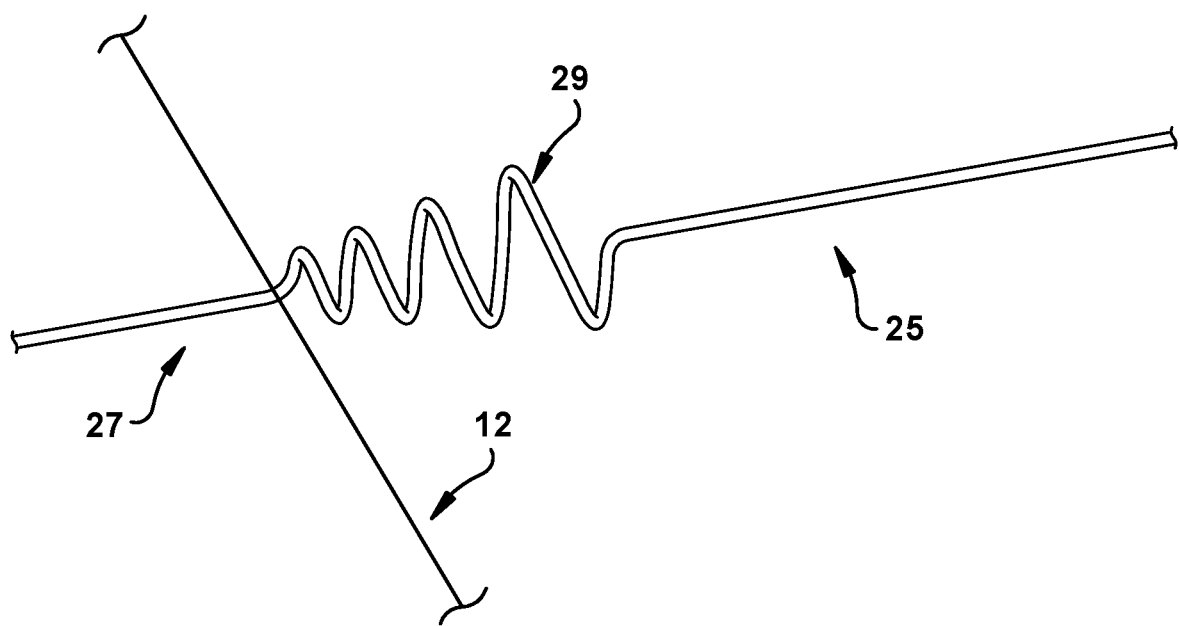
FIG. 17 is a schematic illustration showing an alternative configuration of the microwire body in FIGS. 2A-B, and in particular the anchoring end thereof, partly implanted in a fascicle.

In another aspect, the intrafascicular neural electrode 21 can be implanted in a fascicle 12 as shown in FIG. 17. In this instance, the microwire body 23 can be inserted into the fascicle so that only the distal end 27 is embedded therein.

The middle anchoring portion 29, which remains outside of the fascicle, functions to prevent pullout of the neural electrode 21 once implanted.

The following example is for the purpose of illustration only and is not intended to limit the scope of the claims, which are appended hereto.

EXAMPLE

Figure 18:
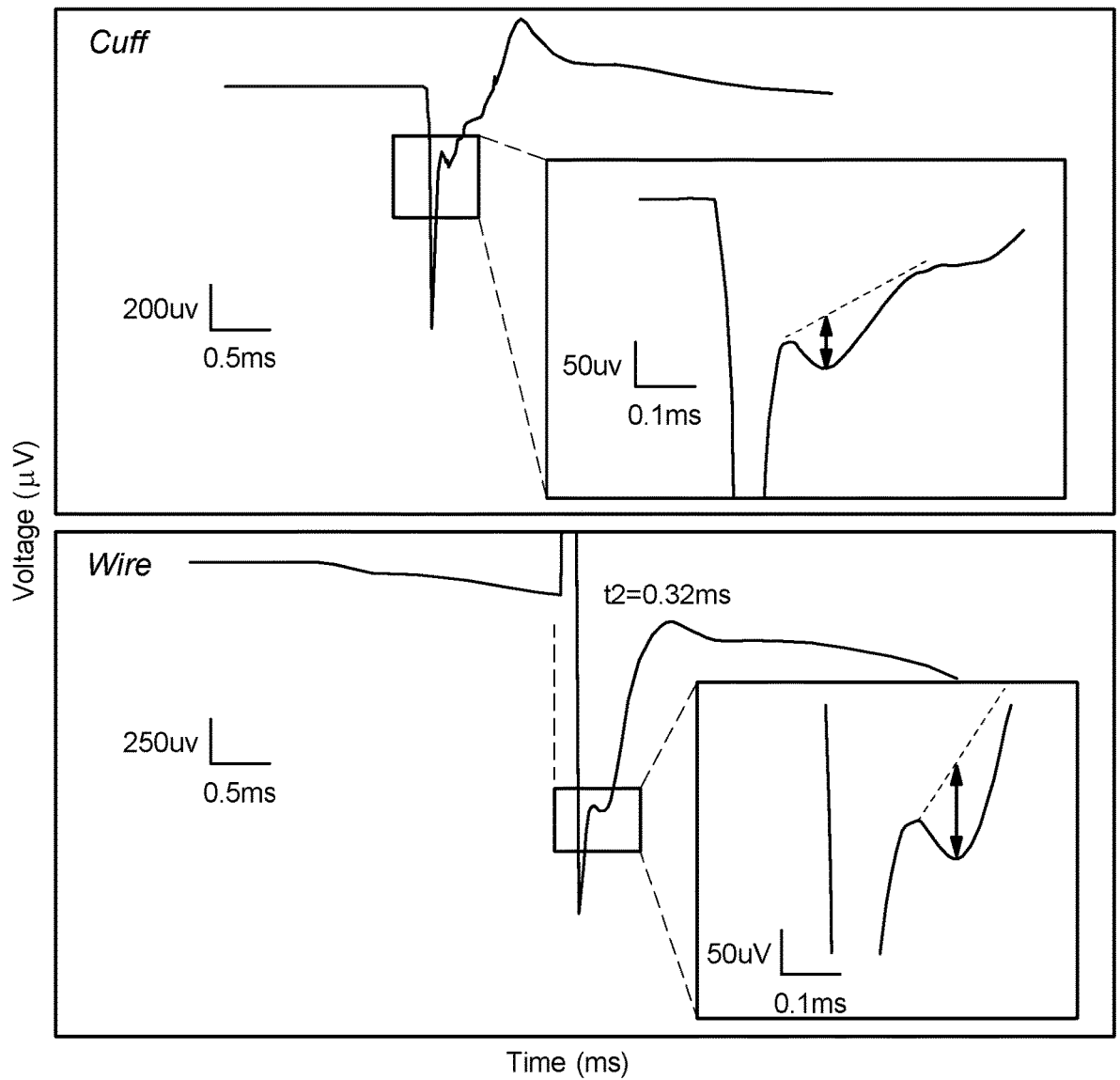
FIG. 18 is a set of graphs comparing results of recorded waveforms and showing that an intrafascicular neural electrode of the present disclosure improves signal amplitudes by a factor of two.

In an acute rat preparation, we inserted a 10 μm diameter platinum-iridium wire into the sciatic nerve using a tungsten microneedle used for microneurography. Stimulation was applied and the compound action potential was recorded using both a cuff electrode and neural electrodes 20 (microwires) of the present disclosure made of platinum-iridium or carbon nanotubes. As compared to a cuff electrode, the neural electrodes 20 increased the signal-to-noise ratio by a factor of two and the recording was stable over several hours (FIG. 18).

Figure 16:
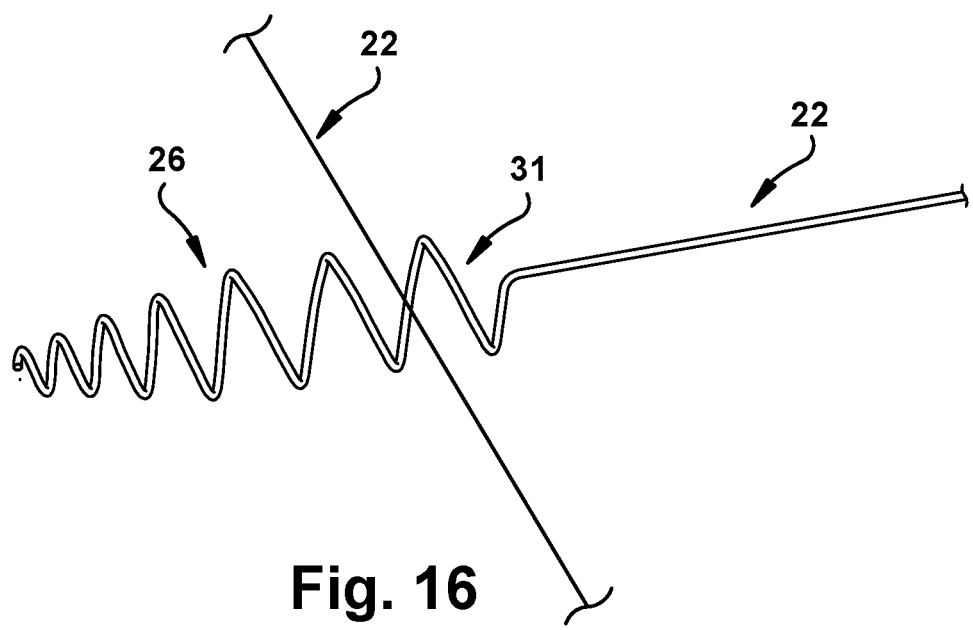
FIG. 16 is a schematic illustration showing an alternative configuration of the microwire body in FIG. 15 partly implanted in a fascicle.

From the above description, those skilled in the art will perceive improvements, changes and modifications. For example, it will be appreciated that the needle introducer 62 can include additional features to facilitate implantation of a neural electrode 20, 90, such as a longitudinal groove (not shown) or lumen (not shown) extending along or through, respectively, the length of the needle introducer. Additionally, it will be appreciated that the distal anchoring end 26 may not include the extension portion 36 (FIG. 16) so that the distal anchoring end terminates at the end of the spiral. Such improvements, changes, and modifications are within the skill of one in the art and are intended to be covered by the appended claims. All patents, patent applications, and publications cited herein are incorporated by reference in their entirety.

The following is claimed:

1. An intrafascicular neural electrode comprising:
a microwire body having a proximal end, a distal end, and a middle anchoring portion extending between the proximal end and the distal end, wherein the middle anchoring portion has a spiral shape with turns that decrease in diameter from the proximal end to the distal end and the distal end has a straight, non-spiral shape,
wherein the proximal end is coated with an insulation material and the distal end is not coated with the insulation material, and
wherein a flexural rigidity of the distal end is adapted to match a flexural rigidity of a target nerve.

2. The intrafascicular neural electrode of claim 1, wherein all or only a portion of the microwire body has a flattened cross-sectional profile.

3. The intrafascicular neural electrode of claim 2, the microwire body being made of graphene.

4. The intrafascicular neural electrode of claim 1, wherein the microwire body, except for the distal end, is coated with the insulation material.

5. The intrafascicular neural electrode of claim 1, wherein a biocompatible agent is adsorbed onto the insulation material.

6. The intrafascicular neural electrode of claim 5, wherein the biocompatible agent is collagen.

7. The intrafascicular neural electrode of claim 1, wherein only the proximal end is coated with the insulation material.

8. The intrafascicular neural electrode of claim 1, wherein the proximal end and a portion of the middle anchoring portion are coated with the insulation material.

9. The intrafascicular neural electrode of claim 1, wherein the distal end and the middle anchoring portion are not coated with the insulation material.

10. A method for implanting a neural electrode in a fascicle comprising a target nerve, the method comprising the steps of:
providing a microwire assembly that includes a proximal end, a distal end, and a middle anchoring portion extending between the proximal end and the distal end, a flexural rigidity of the distal end matching a flexural rigidity of the target nerve,
wherein the middle anchoring portion has a spiral shape with turns that decrease in diameter from the proximal end to the distal end and the distal end has a straight, non-spiral shape, and
wherein the proximal end is coated with an insulation material and the distal end is not coated with the insulation material; and
inserting a portion of the microwire assembly into the fascicle so that the distal end, but not the middle anchoring portion, is embedded therein.

* * * * *